(12) United States Patent
Katz et al.

(10) Patent No.: US 6,670,168 B1
(45) Date of Patent: Dec. 30, 2003

(54) **RECOMBINANT *STREPTOMYCES HYGROSCOPICUS* HOST CELLS THAT PRODUCE 17-DESMETHYLRAPAMYCIN**

(75) Inventors: Leonard Katz, Oakland, CA (US); Lu Liu, Redwood City, CA (US); Loleta M. Chung, San Francisco, CA (US)

(73) Assignee: Kosan Bioscience, Inc., Hayward, CA (US)

( * ) Notice: Subject to any disclaimer, the term of this patent is extended or adjusted under 35 U.S.C. 154(b) by 82 days.

(21) Appl. No.: 09/702,029

(22) Filed: Oct. 30, 2000

Related U.S. Application Data
(60) Provisional application No. 60/198,578, filed on Apr. 20, 2000, and provisional application No. 60/162,229, filed on Oct. 29, 1999.

(51) Int. Cl.$^7$ ................................ C12N 1/20
(52) U.S. Cl. ................................ 435/252.35
(58) Field of Search .................... 435/252.35

(56) References Cited

U.S. PATENT DOCUMENTS

| | | | |
|---|---|---|---|
| 5,672,491 A | 9/1997 | Khosla et al. | 435/148 |
| 5,824,513 A | 10/1998 | Katz et al. | 435/76 |
| 5,962,290 A | 10/1999 | Khosla et al. | 435/183 |
| 6,066,721 A | 5/2000 | Khosla et al. | 536/23.1 |
| 6,080,555 A | 6/2000 | Khosla et al. | 435/41 |
| 6,200,813 B1 * | 3/2001 | Katz et al. | 435/477 |

FOREIGN PATENT DOCUMENTS

| | | |
|---|---|---|
| EP | 0 510 904 | 10/1992 |
| WO | WO 93/16189 | 8/1993 |
| WO | WO 95/22972 | 8/1995 |
| WO | WO 98/01546 | 1/1998 |
| WO | WO 98/49315 | 11/1998 |
| WO | WO 98/54308 | 12/1998 |
| WO | WO 00/20601 | 3/2000 |

OTHER PUBLICATIONS

Aparacio, J. et al. (1996) *Gene* 169:9–16.
Schwecke, T. et al. (1995) *Proc Natl Acad Sci USA* 92:7839–7843.
Lomovskaya et al., Microbiology (1997) 143:875–883.
Nelson et al., Bioorganic & Medicinal Chemistry (1999) 9(2):295–300.
Ruan et al., Gene (1997) 203:1–9.

\* cited by examiner

*Primary Examiner*—Rebecca E. Prouty
*Assistant Examiner*—Kathleen Kerr
(74) *Attorney, Agent, or Firm*—Morrison & Foerster LLP

(57) ABSTRACT

Recombinant host cells that produce rapamycin analogues are constructed by deleting or modifying rapamycin biosynthetic gene cluster genes and are useful in the production of compounds used as antifungals, anticancers, immunosuppressants, and neurotrophins.

1 Claim, 2 Drawing Sheets

Biosynthesis of 6-Deoxyerythronolide B (6-dEB), the Aglycone of Erythromycin, by a Modular PKS

RECOMBINANT *STREPTOMYCES HYGROSCOPICUS* HOST CELLS THAT PRODUCE 17-DESMETHYLRAPAMYCIN

CROSS-REFERENCE TO RELATED APPLICATION

This patent application claims priority to provisional U.S. patent application Ser. Nos. 60/162,229, filed Oct. 29, 1999, and Ser. No. 60/198,578, filed Apr. 20, 2000, both of which are incorporated herein by reference.

FIELD OF THE INVENTION

The present invention provides recombinant methods and materials for producing novel polyketides by recombinant DNA technology. The invention relates to the fields of agriculture, animal husbandry, chemistry, medicinal chemistry, medicine, molecular biology, pharmacology, and veterinary technology.

BACKGROUND OF THE INVENTION

Polyketides represent a large family of diverse compounds synthesized from 2-carbon units through a series of condensations and subsequent modifications. Polyketides occur in many types of organisms, including fungi and mycelial bacteria, in particular, the actinomycetes. There are a wide variety of polyketide structures, and the class of polyketides encompasses numerous compounds with diverse activities. Erythromycin, FK-506, FK-520, megalomicin, narbomycin, oleandomycin, picromycin, rapamycin, spinocyn, and tylosin are examples of such compounds. Given the difficulty in producing polyketide compounds by traditional chemical methodology, and the typically low production of polyketides in wild-type cells, there has been considerable interest in finding improved or alternate means to produce polyketide compounds. See PCT publication Nos. WO 93/13663; WO 95/08548; WO 96/40968; 97/02358; and 98/27203; U.S. Pat. Nos. 4,874, 748; 5,063,155; 5,098,837; 5,149,639; 5,672,491; and 5,712,146; Fu et al., 1994, *Biochemistry* 33: 9321–9326; McDaniel et al., 1993, Science 262: 1546–1550; and Rohr, 1995, *Angew. Chem. Int. Ed. Engl.* 34(8): 881–888, each of which is incorporated herein by reference.

Polyketides are synthesized in nature by polyketide synthase (PKS) enzymes. These enzymes, which are complexes of multiple large proteins, are similar to the synthases that catalyze condensation of 2-carbon units in the biosynthesis of fatty acids. PKS enzymes are encoded by PKS genes that usually consist of three or more open reading frames (ORFs). Two major types of PKS enzymes are known; these differ in their composition and mode of synthesis. These two major types of PKS enzymes are commonly referred to as Type I or "modular" and Type II "iterative" PKS enzymes.

Modular PKSs are responsible for producing a large number of 12-, 14-, and 16-membered macrolide antibiotics including erythromycin, megalomicin, methymycin, narbomycin, oleandomycin, picromycin, and tylosin. Each ORF of a modular PKS can comprise one, two, or more "modules" of ketosynthase activity, each module of which consists of at least two (if a loading module) and more typically three (for the simplest extender module) or more enzymatic activities or "domains." These large multifunctional enzymes (>300,000 kDa) catalyze the biosynthesis of polyketide macrolactones through multistep pathways involving decarboxylative condensations between acyl thioesters followed by cycles of varying β-carbon processing activities (see O'Hagan, D. The polyketide metabolites; E. Horwood: New York, 1991, incorporated herein by reference).

During the past half decade, the study of modular PKS function and specificity has been greatly facilitated by the plasmind-based Streptomyces coelicolor expression system developed with the 6-deoxyerythronolide B (6-dEB) synthase (DEBS) genes (see Kao et al., 1994, *Science*, 265: 509–512, McDaniel et al., 1993, *Science* 262: 1546–1557, and U.S. Pat. Nos. 5,672,491 and 5,712,146, each of which is incorporated herein by reference). The advantages to this plasmid-based genetic system for DEBS are that it overcomes the tedious and limited techniques for manipulating the natural DEBS host organism, *Saccharopolyspora erythraea*, allows more facile construction of recombinant PKSs, and reduces the complexity of PKS analysis by providing a "clean" host background. This system also expedited construction of the first combinatorial modular polyketide library in Streptomyces (see PCT publication No. WO 98/49315, incorporated herein by reference).

The ability to control aspects of polyketide biosynthesis, such as monomer selection and degree of β-carbon processing, by genetic manipulation of PKSs has stimulated great interest in the combinatorial engineering of novel antibiotics (see Hutchinson, 1998, *Curr. Opin. Microbiol.* 1: 319–329; Carreras and Santi, 1998, *Curr. Opin. Biotech.* 9: 403411; and U.S. Pat. Nos. 5,712,146 and 5,672,491, each of which is incorporated herein by reference). This interest has resulted in the cloning, analysis, and manipulation by recombinant DNA technology of genes that encode PKS enzymes. The resulting technology allows one to manipulate a known PKS gene cluster either to produce the polyketide synthesized by that PKS at higher levels than occur in nature or in hosts that otherwise do not produce the polyketide. The technology also allows one to produce molecules that are structurally related to, but distinct from, the polyketides produced from known PKS gene clusters.

Rapamycin is a macrocyclic polyketide that is produced by *Streptomyces hygroscopicus* (ATCC 29253, NRRL 5491) and Actinoplanes sp. N902-109 (see Drugs and the Pharmaceutical Sciences, Vol. 82, Biotechnology of Antibiotics, 2d Ed., ed. W. R. Strohl, Chapter 17, incorporated herein by reference). Rapamycin has antifungal, antitumor, and potent immunosuppressant activities, and is of significant interest for the treatment of autoimmune disease and prevention of rejection of organ and skin allografts (see Schwecke et al., August 1995, *Proc. Natl. Acad. Sci. USA* 92: 7839–7845, and references cited therein, incorporated herein by reference). The immunosuppressant activity arises from the ability of rapamycin to prevent the proliferative response of T cells to interleukin 2 bound at the interleukin 2 receptor (see Schwecke et al., supra). Hence, rapamycin offers an exciting opportunity to develop new classes of antifungal, antitumor, and immunosuppressant drugs The number and diversity of rapamycin derivatives have been-limited due to the limited number of chemical modifications that can be performed on the complex molecule and the unavailability of recombinant host cells that produce rapamycin analogs. Genetic systems that result from engineering of the rapamycin biosynthetic genes would be valuable for creating novel compounds for pharmaceutical, agricultural, and veterinary applications. The production of such compounds could be more readily accomplished if recombinant host cells producing diverse rapamycin analogs were available. The present invention meets these and other needs.

SUMMARY OF THE INVENTION

The present invention provides recombinant methods and materials for expressing PKS enzymes and polyketide modification enzymes derived in whole and in part from the rapamycin biosynthetic genes in recombinant host cells. The invention also provides the polyketides produced by such PKS enzymes. Thus, in one embodiment, the invention is directed to recombinant materials comprising nucleic acids with nucleotide sequences encoding the rapamycin biosynthetic genes in which at least one domain, module, or protein encoded by a rapamycin PKS gene has been deleted, rendered inactive by mutation, or replaced by a different domain, module, or protein coding sequence.

In one embodiment, the invention provides recombinant host cells that produce a rapamycin derivative or analogue. In one embodiment, the rapamycin analogue is produced by a recombinant host cell that expresses a hybrid PKS comprising all or part of the rapamycin PKS and at least a part of a second PKS.

In a preferred embodiment, the host cell is *Streptomyces hygroscopicus*.

The invention also provides novel polyketides, antitumor agents, antifungal agents, immunosuppressants and other useful compounds derived therefrom. The compounds of the invention can also be used in the manufacture of another compound. In a preferred embodiment, the compounds of the invention are formulated in a mixture or solution for administration to an animal or human.

These and other embodiments of the invention are described in more detail in the following description, the examples, and claims set forth below.

DETAILED DESCRIPTION OF THE INVENTION

The present invention provides useful compounds and methods for producing polyketides in recombinant host cells. As used herein, the term recombinant refers to a compound or composition produced by human intervention. The invention provides recombinant DNA compounds encoding all or a portion of the rapamycin biosynthetic genes. The invention provides recombinant expression vectors useful in producing the rapamycin PKS and hybrid PKSs composed of a portion of the rapamycin PKS in recombinant host cells. The invention also provides the polyketides produced by the recombinant PKS and polyketide modification enzymes.

Rapamycin belongs to the polyketide class of natural products whose members have diverse structural and pharmacological properties (see Monaghan and Tkacz, 1990, *Annu. Rev. Microbiol.* 44: 271, incorporated herein by reference). Rapamycin is assembled by a polyketide synthase (PKS) enzyme. These enzymes mediate successive condensations of activated coenzyme-A thioester monomers derived from small organic acids such as acetate, propionate, and butyrate. Active sites required for condensation include an acyltransferase (AT), acyl carrier protein (ACP), and beta-ketoacylsynthase (KS). Each condensation cycle results in a β-keto group that undergoes all, some, or none of a series of processing activities. Active sites that perform these reactions include a ketoreductase (KR), dehydratase (DH), and enoylreductase (ER). Thus, the absence of any beta-keto processing domain results in the presence of a ketone, a KR alone gives rise to a hydroxyl, a KR and DH result in an alkene, while a KR, DH, and ER combination leads to complete reduction to an alkane. After assembly of the polyketide chain, the molecule typically undergoes cyclization(s) and post-PKS modification (e.g. glycosylation, oxidation, acylation) to achieve the final active compound.

Figure 1:
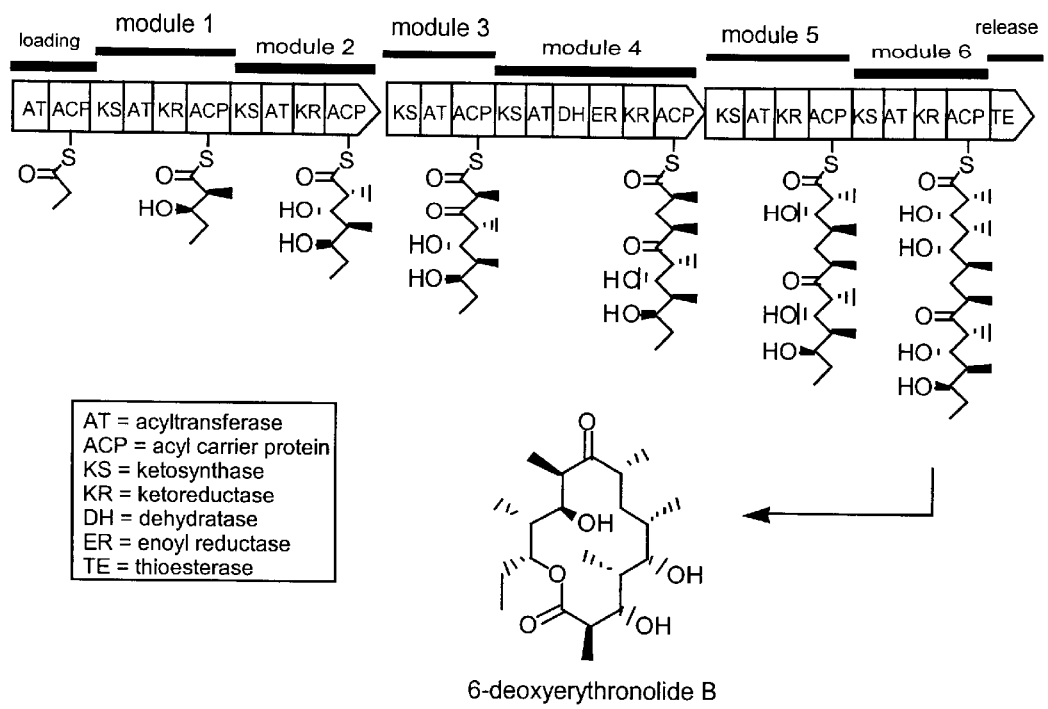
FIG. 1 shows the modules and domains of DEBS.

Macrolides such as erythromycin and rapamycin are synthesized by modular PKSs (see Cane et al., 1998, *Science* 282: 63, incorporated herein by reference). For illustrative purposes, the PKS that produces the erythromycin polyketide (6-deoxyerythronolide B synthase or DEBS; see U.S. Pat. No. 5,824,513, incorporated herein by reference) is shown in FIG. 1. DEBS is the most characterized and extensively used modular PKS system. DEBS synthesizes the polyketide 6-deoxyerythronolide B (6-dEB). In modular PKS enzymes such as DEBS, the enzymatic steps for each round of condensation and reduction are encoded within a single "module" of the polypeptide (i.e., one distinct module for every condensation cycle). DEBS consists of a loading module and 6 extender modules and a chain terminating thioesterase (TE) domain within three extremely large polypeptides encoded by three open reading frames (ORFs, designated enyAI, enyAII, and eryAIII).

Each of the three polypeptide subunits of DEBS (DEBSI, DEBSII, and DEBSIII) contains 2 extender modules; DEBSI additionally contains the loading module. Collectively, these proteins catalyze the condensation and appropriate reduction of 1 propionyl CoA starter unit and 6 methylmalonyl CoA extender units. Extender modules 1, 2, 5, and 6 contain KR domains; module 4 contains a complete set, KR/DH/ER, of reductive and dehydratase domains; and module 3 contains no functional reductive domain. Following the condensation and appropriate dehydration and reduction reactions, the enzyme bound intermediate is lactonized by the TE at the end of extender module 6 to form 6-dEB.

More particularly, the loading module of DEBS consists of two domains, an acyl-transferase (AT) domain and an acyl carrier protein (ACP) domain. In other PKS enzymes, the loading module is not composed of an AT and an ACP but instead utilizes an inactivated KS, an AT, and an ACP. This inactivated KS is in most instances called $KS^Q$, where the superscript letter is the abbreviation for the amino acid, glutamine, that is present instead of the active site cysteine required for activity. The AT domain of the loading module recognizes a particular acyl-CoA (propionyl for DEBS, which can also accept acetyl) and transfers it as a thiol ester to the ACP of the loading module. Concurrently, the AT on each of the extender modules recognizes a particular extender-CoA (methylmalonyl for DEBS) and transfers it to the ACP of that module to form a thioester. Once the PKS is primed with acyl- and malonyl-ACPs, the acyl group of the loading module migrates to form a thiol ester (transesterification) at the KS of the first extender module; at this stage, extender module 1 possesses an acyl-KS and a methylmalonyl ACP. The acyl group derived from the loading module is then covalently attached to the alpha-carbon of the malonyl group to form a carbon-carbon bond, driven by concomitant decarboxylation, and generating a new acyl-ACP that has a backbone two carbons longer than the loading unit (elongation or extension). The growing polyketide chain is transferred from the ACP to the KS of the next module, and the process continues.

The polyketide chain, growing by two carbons each module, is sequentially passed as a covalently bound thiol ester from module to module, in an assembly line-like process. The carbon chain produced by this process alone would possess a ketone at every other carbon atom, producing a polyketone, from which the name polyketide arises. Commonly, however, the beta keto group of each two-carbon unit is modified just after it has been added to the growing polyketide chain but before it is transferred to the next module by either a KR, a KR plus a DH, or a KR, a DH, and an ER. As noted above, modules may contain additional enzymatic activities as well.

Once a polyketide chain traverses the final extender module of a PKS, it encounters the releasing domain or thioesterase found at the carboxyl end of most PKSs. Here, the polyketide is cleaved from the enzyme and cyclyzed. The resulting polyketide can be modified further by tailoring or modification enzymes; these enzymes add carbohydrate groups or methyl groups, or make other modifications, i.e., oxidation or reduction, on the polyketide core molecule.

For example, the final steps in conversion of 6-dEB to erythromycin A include the actions of a number of modification enzymes, such as: C-6 hydroxylation, attachment of mycarose and desosamine sugars, C-12 hydroxylation (which produces erythromycin C), and conversion of mycarose to cladinose via O-methylation.

With this overview of the DEBS PKS, one can better appreciate the somewhat more complex rapamycin PKS (RAPS for rapamycin synthase) and rapamycin modification enzymes. The genes that encode the PKS and the modification enzymes are collectively referred to herein as the rapamycin biosynthetic gene cluster. The rapamycin biosynthetic gene cluster was first described by Schwecke et al., supra. This reference reported that the PKS was composed of three proteins, RAPS1, RAPS2, and RAPS3, encoded by three genes, rapA, rapB, and rapC, respectively. RAPS1 comprised the loading module (also referred to as a loading domain) and four extender modules (1 through 4).

RAPS2 encoded six extender modules (5 through 10). RAPS3 encoded four extender modules (11 through 14).

The loading module of RAPS is somewhat more unusual than that of DEBS in that it comprises a coenzyme A (CoA) ligase domain, an ACP domain, an ER domain. The CoA domain binds a shikimic acid derivative ((4R,5R)-dihydroxycyclohex-1-enecarboxylic acid) that is reduced by the ER domain to provide the (1R,3R,4R)-dihydroxycyclohexanecarboxylic acid starter unit.

The extender modules of RAPS all comprise KS, AT, and ACP domains. The specificities of the AT domains and the presence of KR, DH, and ER domains in each of the extender modules are identified in the table below (see Aparicio et al., 1996, Gene 169: 9–16, incorporated herein by reference).

| Extender Module | AT Specificity | KR, DH, and ER Domains |
|---|---|---|
| 1 | Methylmalonyl CoA | KR, DH, ER |
| 2 | Malonyl CoA | KR (inactive) |
| 3 | Methylmalonyl CoA | KR, DH, ER |
| 4 | Methylmalonyl CoA | KR, DH |
| 5 | Malonyl CoA | KR |
| 6 | Methylmalonyl CoA | KR (inactive), DH |
| 7 | Methylmalonyl CoA | KR, DH, ER |
| 8 | Malonyl CoA | KR, DH |
| 9 | Malonyl CoA | KR, DH |
| 10 | Methylmalonyl CoA | KR, DH |
| 11 | Malonyl CoA | KR |

-continued

| Extender Module | AT Specificity | KR, DH, and ER Domains |
|---|---|---|
| 12 | Malonyl CoA | KR |
| 13 | Methylmalonyl CoA | KR, DH, ER |
| 14 | Malonyl CoA | None |

As described more fully below, the present invention provides novel PKS enzymes that differ from RAPS in that the AT specificity and/or the presence or absence of KR, DH, and/or ER domains of at least one of the extender modules is different.

RAPS is also somewhat more unusual than DEBS in that it does not contain a TE domain that cyclizes the polyketide. Instead, in RAPS, cyclization is mediated by the rapP gene product. Thus, the polyketide chain of rapamycin is transferred from RAPS3 to the amino group of a RAPP bound pipecolyl moiety, and the macrolactam ring is formed by attack of the C-34 hydroxyl at the carboxyl group of the pipecolyl moiety. The pipecolyl moiety is formed by a lysine cyclodeaminase encoded by the rapL gene in the rapamycin biosynthetic gene cluster. In one aspect, the present invention provides recombinant host cells derived from rapamycin producing host cells in which the rapL gene has been rendered inactive by deletion or mutation. Such host cells can then be provided with either D,L-pipecolic acid, to make rapamycin, or pipecolic acid -derivatives or other compounds capable of serving as substrates for the rapP gene product, to make rapamycin derivatives. Such host cells can also be used to express rapamycin PKS derivatives (including those formed by deletion or inactivation of a domain or domains and those formed by replacement of a domain or domains with a domain or domains from a heterologous PKS), again either by feeding D,L-pipecolic acid, pipecolic acid derivatives, or other compounds capable of serving as substrates for the rapP gene product. Such other compounds include, for example and without limitation, L-proline and its derivatives.

Once the rapamycin macrolactam ring has been formed, a number of other rapamycin modification enzymes act on the compound to form rapamycin. To facilitate discussion of these enzymes and the genes that encode them, the structure of rapamycin is shown below.

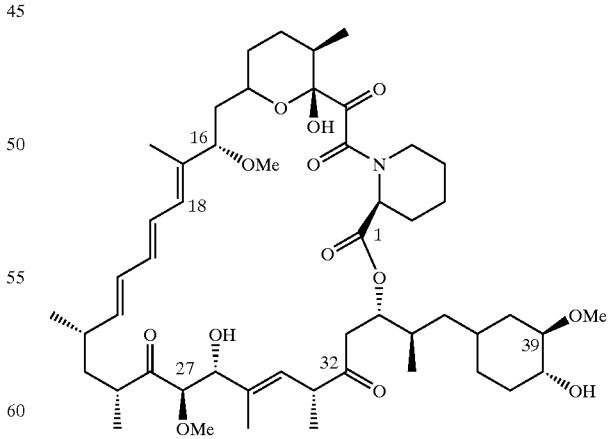

Rapamycin modification enzymes methylate the hydroxyl groups at C-16 and C-39 to form the C-16 and C-39 methoxy groups, oxidize C-9 to form the C-9 keto group, oxidize C-27 to form a hydroxyl, and then methylate the C-27 hydroxyl to form the C-27 methoxy.

The genes that encode these modification enzymes have also been cloned and characterized. See Drugs and the Pharmaceutical Sciences, Vol. 82, supra, and Molnar et al., 1996, *Gene* 169: 1–7, each of which is incorporated herein by reference. Thus, the rapI gene product methylates the C-39 hydroxyl group to form the C-39 methoxy group. The rapJ gene product is a P450 enzyme that oxidizes C-9 to form the C-9 keto group. The rapN gene product, a P450 enzyme, and the rapO gene product, a ferredoxin, together oxidize C-27 to, in effect, attach a hydroxyl group at that position. The rapM and rapQ gene products are methyltransferases that methylate the C-16 and C-27 hydroxyl groups.

The present invention provides recombinant host cells that are derived from rapamycin producing host cells and differ therefrom by inactivation of one or more of the rapI, rapJ, rapM, rapN, rapO, and rapQ genes. As mentioned above, these host cells also include those in which the rapL gene has also been inactivated. Illustrative host cells of the invention include host cells derived from *Streptomyces hygroscopicus* ATCC 29253 in which the genes indicated have been inactivated: (i) rapI, (ii) rapJ, (iii) rapM, (iv) rapQ, (v) rapN, and rapO, (vi) rapM, rapN, rapO, (vii) rapN, rapO, and rapQ, (viii) rapM, rapN, rapO, and rapQ, and (ix) rapL, rapM, rapN, rapO, and rapQ. The invention also provides such host cells that also express rapamycin PKS derivatives, as noted above and exemplified below.

One illustrative recombinant host cell provided by the present invention expresses a recombinant rapamycin PKS in which the extender module 1 KS domain is inactivated by deletion or other mutation. In a preferred embodiment, the inactivation is mediated by a change in the KS domain that renders it incapable of binding substrate (called a KS1° mutation). In a particularly preferred embodiment, this inactivation is rendered by a mutation in the codon for the active site cysteine that changes the codon to another codon, such as an alanine codon. Host cells expressing, or cell free extracts containing, a PKS comprising the protein encoded thereby can be fed or supplied with N-acylcysteamine thioesters of precursor molecules to prepare a polyketide of interest. See U.S. patent application Ser. No. 09/492,733, filed Jan. 27, 2000, and PCT patent publication Nos. US99/03986 and US00/44717, each of which are incorporated herein by reference. Such KS1° constructs of the invention are useful in the production of rapamycin analogs of the invention that differ from rapamycin in the composition of the starter unit.

The recombinant host cells of the invention include those in which coding sequences for one or more domains or modules of the rapamycin PKS have been deleted by homologous recombination. Thus, the invention provides a variety of modified rapamycin producing host cells in which one or more of the rapamycin biosynthetic genes have been mutated or disrupted. These cells are useful when it is desired to replace the disrupted function with a gene product expressed by a recombinant DNA expression vector. Illustrative expression vectors of the invention are described in more detail below. Such host cells can be preferred host cells for expressing rapamycin analogs of the invention. Particularly preferred host cells of this type include those in which the coding sequence for the loading module has been mutated or disrupted, those in which one or more of any of the PKS gene ORFs has been mutated or disrupted, and/or those in which the genes for one or more modification enzymes have been mutated or disrupted.

While the present invention provides many useful recombinant host cells derived from rapamycin producing host cells such as Streptomyces hygroscopicus, the rapamycin analogs of the present invention can also be produced in heterologous hosts by expression of all or a portion of the rapamycin biosynthetic gene. In one embodiment, the invention provides methods for the heterologous expression of one or more of the rapamycin biosynthetic genes and recombinant DNA expression vectors useful in the method. For purposes of the invention, any host cell other than a naturally occurring rapamycin producing host cell is a heterologous host cell. Thus, included within the scope of the invention are recombinant expression vectors that include such nucleic acids.

The term expression vector, as used herein, refers to a nucleic acid that can be introduced into a host cell or cell-free transcription and translation system. An expression vector can be maintained permanently or transiently in a cell, whether as part of the chromosomal or other DNA in the cell or in any cellular compartment, such as a replicating vector in the cytoplasm. An expression vector also comprises a promoter that drives expression of an RNA, which typically is translated into a polypeptide in the cell or cell extract. For efficient translation of RNA into protein, the expression vector also typically contains a ribosome-binding site sequence positioned upstream of the start codon of the coding sequence of the gene to be expressed. Other elements, such as enhancers, secretion signal sequences, transcription termination sequences, and one or more marker genes by which host cells containing the vector can be identified and/or selected, may also be present in an expression vector. Selectable markers, i.e., genes that confer antibiotic resistance or sensitivity, are preferred and confer a selectable phenotype on transformed cells when the cells are grown in an appropriate selective medium.

The various components of an expression vector can vary widely, depending on the intended use of the vector and the host cell(s) in which the vector is intended to replicate or drive expression. Expression vector components suitable for the expression of genes and maintenance of vectors in *E. coli*, yeast, Streptomyces, and other commonly used cells are widely known and commercially available. For example, suitable promoters for inclusion in the expression vectors of the invention include those that function in eucaryotic or procaryotic host cells. Promoters can comprise regulatory sequences that allow for regulation of expression relative to the growth of the host cell or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433), can also be used.

Thus, recombinant expression vectors contain at least one expression system, which, in turn, is composed of at least a portion of the rapamycin PKS and/or other rapamycin biosynthetic gene coding sequences operably linked to a promoter and optionally termination sequences that operate to effect expression of the coding sequence in compatible host cells. The host cells are modified by transformation with the recombinant DNA expression vectors of the invention to contain the expression system sequences either as extrachromosomal elements or integrated into the chromosome. The resulting host cells of the invention are useful in methods to produce PKS and post-PKS modification enzymes as well as polyketides and antibiotics and other useful compounds derived therefrom.

Preferred host cells for purposes of selecting vector components for expression vectors of the present invention include fungal host cells such as yeast and procaryotic host cells such as E. coli and Streptomyces, but mammalian host cells can also be used. In hosts such as yeasts, plants, or mammalian cells that ordinarily do not produce polyketides, it may be necessary to provide, also typically by recombinant means, suitable holo-ACP synthases to convert the recombinantly produced PKS to functionality. Provision of such enzymes is described, for example, in PCT publication Nos. WO 97/13845 and 98/27203, each of which is incorporated herein by reference. Particularly preferred host cells for purposes of the present invention are Streptomyces and Saccharopolyspora host cells, as discussed in greater detail below.

In a preferred embodiment, the expression vectors of the invention are used to construct a heterologous recombinant Streptomyces host cell that expresses a recombinant PKS of the invention. Streptomyces is a convenient host for expressing polyketides, because polyketides are naturally produced in certain Streptomyces species, and Streptomyces cells generally produce the precursors needed to form the desired polyketide. Those of skill in the art will recognize that, if a Streptomyces host cell produces any portion of a PKS enzyme or produces a polyketide modification enzyme, the recombinant vector need drive expression of only those genes constituting the remainder of the desired PKS enzyme or other polyketide-modifying enzymes. Thus, such a vector may comprise only a single ORF, with the desired remainder of the polypeptides constituting the PKS provided by the genes on the host cell chromosomal DNA.

If a Streptomyces or other host cell ordinarily produces polyketides, it may be desirable to modify the host so as to prevent the production of endogenous polyketides prior to its use to express a recombinant PKS of the invention. Such modified hosts include S. coelicolor CH999 and similarly modified S. lividans described in U.S. Pat. No. 5,672,491, and PCT publication Nos. WO 95/08548 and WO 96/40968, incorporated herein by reference. In such hosts, it may not be necessary to provide enzymatic activities for all of the desired post-translational modifications of the enzymes that make up the recombinantly produced PKS, because the host naturally expresses such enzymes. In particular, these hosts generally contain holo-ACP synthases that provide the phosphopantotheinyl residue needed for functionality of the PKS.

The invention provides a wide variety of expression vectors for use in Streptomyces. The replicating expression vectors of the present invention include, for example and without limitation, those that comprise an origin of replication from a low copy number vector, such as SCP2*(see Hopwood et al., Genetic Manipulation of Streptomyces: A Laboratory manual (The John Innes Foundation, Norwich, U.K., 1985); Lydiate et al., 1985, Gene 35: 223–235; and Kieser and Melton, 1988, Gene 65: 83–91, each of which is incorporated herein by reference), SLP1.2 (Thompson et al., 1982, Gene 20: 51–62, incorporated herein by reference), and pSG5(ts) (Muth et al., 1989, Mol. Gen. Genet. 219: 341–348, and Bierman et al., 1992, Gene 116: 4349, each of which is incorporated herein by reference), or a high copy number vector, such as pIJ101 and pjV1 (see Katz et al., 1983, J. Gen. Microbiol. 129: 2703–2714; Vara et al., 1989, J. Bacteriol. 171: 5782–5781; and Servin-Gonzalez, 1993, Plasmid 30: 131–140, each of which is incorporated herein by reference). High copy number vectors are, however, generally not preferred for expression of large genes or multiple genes. For non-replicating and integrating vectors and generally for any vector, it is useful to include at least an E. coli origin of replication, such as from pUC, p1P, p1I, and pBR. For phage based vectors, the phage phiC31 and its derivative KC515 can be employed (see Hopwood et al., supra). Also, plasmid pSET152, plasmid pSAM, plasmids pSE101 and pSE211, all of which integrate site-specifically in the chromosomal DNA of S. lividans, can be employed for purposes of the present invention.

The Streptomyces recombinant expression vectors of the invention typically comprise one or more selectable markers, including antibiotic resistance conferring genes selected from the group consisting of the ermE (confers resistance to erythromycin and lincomycin), tsr (confers resistance to thiostrepton), aadA (confers resistance to spectinomycin and streptomycin), aacC4 (confers resistance to apramycin, kanamycin, gentamicin, geneticin (G418), and neomycin), hyg (confers resistance to hygromycin), and vph (confers resistance to viomycin) resistance conferring genes. Alternatively, several polyketides are naturally colored, and this characteristic can provide a built-in marker for identifying cells.

The streptomycete bacteria have been widely used for almost 50 years and are excellent hosts for production of rapamycin and its analogs. Streptomyces lividans and S. coelicolor have been developed for the expression of heterologous PKS systems. These organisms can stably maintain cloned heterologous PKS genes, express them at high levels under controlled conditions, and modify the corresponding PKS proteins (e.g., phosphopantotheinylation) so that they are capable of production of the polyketide they encode. Furthermore, these hosts contain the necessary pathways to produce the substrates required for polyketide synthesis; e.g. propionyl-CoA and methylmalonyl-CoA. A wide variety of cloning and expression vectors are available for these hosts, as are methods for the introduction and stable maintenance of large segments of foreign DNA. S. lividans and S. coelicolor grow well on a number of media and have been adapted for high level production of polyketides in fermentors. If production levels are low, a number of rational approaches are available to improve yield (see Hosted and Baltz, 1996, Trends Biotechnol. 14(7) :245–50, incorporated herein by reference). Empirical methods to increase the titers of these macrolides, long since proven effective for numerous bacterial polyketides, can also be employed.

Preferred Streptomyces host cell/vector combinations of the invention include S. coelicolor CH999 and S. lividans K4–114 host cells, which have been modified so as not to produce the polyketide actinorhodin, and expression vectors derived from the pRM1 and pRM5 vectors, as described in U.S. Pat. No. 5,830,750 and U.S. patent application Ser. Nos. 08/828,898, filed Mar. 31, 1997, and Ser. No. 09/181, 833, filed Oct. 28, 1998, each of which is incorporated herein by reference. These vectors are particularly preferred in that they contain promoters compatible with numerous and diverse Streptomyces spp. Particularly useful promoters for Streptomyces host cells include those from PKS gene clusters that result in the production of polyketides as secondary metabolites, including promoters from aromatic (Type II) PKS gene clusters. Examples of Type II PKS gene cluster promoters are act gene promoters and tcm gene promoters; an example of a Type I PKS gene cluster promoter are the promoters of the spiramycin PKS genes and DEBS genes. The present invention also provides the rapamycin biosynthetic gene promoters in recombinant form. These promoters can be used to drive expression of the rapamycin biosynthetic genes or any other coding sequence of interest in host cells in which the promoter functions, particulary *Micromonospora megalomicea* and generally any Streptomyces species.

As described above, particularly useful control sequences are those that alone or together with suitable regulatory systems activate expression during transition from growth to stationary phase in the vegetative mycelium. The promoter contained in the aforementioned plasmid pRM5, i.e., the actI/actIII promoter pair and the actII-ORF4 activator gene, is particularly preferred. Other useful Streptomyces promoters include without limitation those from the ermE gene and the melC1 gene, which act constitutively, and the tipA gene and the merA gene, which can be induced at any growth stage. In addition, the T7 RNA polymerase system has been transferred to Streptomyces and can be employed in the vectors and host cells of the invention. In this system, the coding sequence for the T7 RNA polymerase is inserted into a neutral site of the chromosome or in a vector under the control of the inducible merA promoter, and the gene of interest is placed under the control of the T7 promoter. As noted above, one or more activator genes can also be employed to enhance the activity of a promoter. Activator genes in addition to the actII-ORF4 gene described above include dnrI, redD, and ptpA genes (see U.S. patent application Ser. No. 09/181,833, supra).

To provide a preferred host cell and vector for purposes of the invention, the rapamycin biosynthetic genes are placed on a recombinant expression vector and transferred to the non-macrolide producing hosts *Streptomyces lividans* K4–114 and *S. coelicolor* CH999. Transformation of *S. lividans* K4–114 or *S. coelicolor* CH999 with this expression vector results in a strain which produces detectable amounts of rapamycin as determined by analysis of extracts by LC/MS. The present invention also provides recombinant DNA compounds in which the encoded rapamycin extender module 1 KS domain is inactivated. The introduction into *Streptomyces lividans* or *S. coelicolor* of a recombinant expression vector of the invention that encodes a rapamycin PKS with a KS1° domain produces a host cell useful for making polyketides by a process known as diketide feeding. The resulting host cells can be fed or supplied with N-acylcysteamine thioesters of precursor molecules to prepare rapamycin analogs.

The recombinant host cells of the invention can express all of the rapamycin biosynthetic genes or only a subset of the same. For example, if only the genes for the rapamycin PKS are expressed in a host cell that otherwise does not produce polyketide modifying enzymes that can act on the polyketide produced, then the host cell produces unmodified polyketides, called macrolide aglycones. Such macrolide aglycones can be modified by adding them to the fermentation of a strain such as, for example, *Streptomyces hygroscopicus* that contains the requisite modification enzymes. There are a wide variety of diverse organisms that can modify macrolide aglycones to provide compounds with, or that can be readily modified to have, useful activities. For example, *Saccharopolyspora erythraea, Streptomyces venezuelae, S. narbonensis, Micromonospora megalomicea, Streptomyces antibioticus, S. fradiae,* and *S. thermotolerans* contain polyketide modification enzymes.

In a preferred embodiment, however, the present invention provides methods and genetic constructs for producing the compounds of the invention directly in the host cell of interest. Thus, the recombinant genes of the invention, which include recombinant rapA, rapB, and rapC genes with one or more deletions and/or insertions, including replacements of a rap gene fragment with a gene fragment from a heterologous PKS gene can be included on expression vectors suitable for expression of the encoded gene products in *Streptomyces hygroscopicus* host cells.

Thus, in one important embodiment, the invention provides hybrid PKS enzymes and the corresponding recombinant host cells that produce those hybrid PKS enzymes. For purposes of the invention, a hybrid PKS is a recombinant PKS that comprises all or part of one or more extender modules and/or loading module of the rapamycin PKS and all or part of one or more extender modules and/or loading module of a second PKS. In one preferred embodiment, the second PKS is only a portion of a non-rapamycin PKS, such as DEBS, the FK-506 PKS, and the FK-520 PKS. Illustrative examples of such hybrid PKSs are described below.

Those of skill in the art will recognize that all or part of a hybrid PKS of the invention need not be isolated from a naturally occurring source. For example, only a small portion of an AT domain determines its specificity. See PCT patent publication No. WO US00/01838, and Lau et al., infra, incorporated herein by reference. The state of the art in DNA synthesis allows the artisan to construct de novo DNA compounds of size sufficient to construct a useful portion of a PKS module or domain. Thus, the desired derivative coding sequences can be synthesized using standard solid phase synthesis methods such as those described by Jaye et al., 1984, *J. Biol. Chem.* 259: 6331, and instruments for automated synthesis are available commercially from, for example, Applied Biosystems, Inc. For purposes of the invention, such synthetic DNA compounds are deemed to be a portion of a PKS.

A hybrid PKS of the invention can result not only:
(i) from fusions of heterologous domain (where heterologous means the domains in a module are derived from at least two different naturally occurring modules) coding sequences to produce a hybrid module coding sequence contained in a PKS gene whose product is incorporated into a PKS, but also:
(ii) from fusions of heterologous module (where heterologous module means two modules are adjacent to one another that are not adjacent to one another in naturally occurring PKS enzymes) coding sequences to produce a hybrid coding sequence contained in a PKS gene whose product is incorporated into a PKS,
(iii) from expression of one or more rapamycin PKS genes with one or more non-rapamycin PKS genes, including both naturally occurring and recombinant non-rapamycin PKS genes, and
(iv) from combinations of the foregoing.

Various hybrid PKSs of the invention illustrating these various alternatives are described below.

The present invention also provides rapamycin PKS derivatives that contain no heterologous PKS domains, modules, or proteins, but are instead derived from the rapamycin PKS by inactivation of at least a domain of at least one module. Various examples of rapamycin derivative PKSs are provided below.

The table below shows the rapamycin analogue produced by the hybrid or derivative rapamycin PKS. In each case, the producing host cell is Streptomyces hygroscopicus, and any inactivated rapamycin modification enzyme genes are also indicated. The rapamycin analogs shown in the table are preferred antifungal compounds.

Compound/PKS 17,18-dihydrorapamycin/ER domain inserted in extender module 10

19,20-dihydrorapamycin/ER domain inserted in extender module 9

21,22-dihydrorapamycin/ER domain inserted in extender module 8

17,18,19,20-tetrahydrorapamycin/ER domain inserted in extender module s 9 & 10

17,18,21,29-tetrahydrorapamycin/ER domain inserted in extender modules 8 & 10

19,20,21,22-tetrahydrorapamycin/ER domain inserted in extender modules 8 & 9

17,18,19,20,21,22-hexahydrorapamycin/ER domain inserted in extender modules 8, 9 & 10

16-demethyl-17,18-dihydrorapamycin/Knockout rapamycin 16-O-methyl-transferase; ER domain inserted in extender module 10

16-demethyl-19,20-dihydrorapamycin/Knockout rapamycin 16-O-methyl-transferase; ER domain inserted in extender module 9

16-demethyl-21,22-dihydrorapamycin/Knockout rapamycin 16-O-methyl-transferase; ER domain inserted in extender module 8

16-demethyl-17,18,19,20-tetrahydrorapamycin/Knockout rapamycin 16-O-methyltransferase; ER domain inserted in extender modules 9 & 10

16-demethyl-17,18,21,22-tetrahydrorapamycin/Knockout rapamycin 16-O-methyltransferase; ER domain inserted in extender modules 8 & 10

16-demethyl-19,20,21,22-tetrahydrorapamycin/Knockout rapamycin 16-O-methyltransferase; ER domain inserted in extender module 10

16-demethyl-17,18,19,20,21,22-hexahydrorapamycin/Knockout rapamycin 16-O-methyltranferase; ER domain inserted in extender modules 8, 9 & 10

17-desmethylrapamycin/AT replacement in extender module 10

23-desmethylrapamycin/AT replacement in extender module 7

17,23-didesmethylrapamycin/AT replacements in extender modules 7 & 10

17-desmethyl-17,18-dihydrorapamycin/AT replacement in extender module 10; ER domain inserted in extender module 10

17-desmethyl-19,20-dihydrorapamycin/AT replacement in extender module 10; ER domain inserted in extender module 9

17-desmethyl-21,22-dihydrorapamycin/AT replacement in extender module 10; ER domain inserted in extender module 8

17-desmethyl-17,18,19,20-tetrahydrorapamycin/AT replacement in extender module 10; ER domain inserted in extender modules 9 & 10

17-desmethyl-1 7,18,21,22-tetrahydrorapamycin/AT replacement in extender module 10; ER domain inserted in extender modules 8 & 10

17-desmethyl-19,20,21,22-tetrahydrorapamycin/AT replacement in extender module 10; ER domain inserted in extender modules 8 & 9

17-desmethyl-17,18,19,20,21,22-hexahydrorapamycin/AT replacement in extender module 10; ER domain inserted in extender modules 8, 9 & 10

23-desmethyl-17,18-dihydrorapamycin/AT replacement in extender module 7; ER domain inserted in extender module 10

23-desmethyl-19,20-dihydrorapamycin/AT replacement in extender module 7; ER domain inserted in extender module 9

23-desmethyl-21,22-dihydrorapamycin/AT replacement in extender module 7; ER domain inserted in extender module 8

23-desmethyl-17,18,19,20-tetrahydrorapamycin/AT replacement in extender module 7; ER domain inserted in extender modules 9 & 10

23-desmethyl-17,18,21,22-tetrahydrorapamycin/AT replacement in extender module 7; ER domain inserted in extender modules 8 & 10

23-desmethyl-19,20,21,22-tetrahydrorapamycin/AT replacement in extender module 7; ER domain inserted in extender modules 8, & 9

23-desmethyl-17,18,19,20,21,22-hexahydrorapamycin/AT replacement in extender module 7; ER domain inserted in extender modules 8, 9 & 10

17,23-didesmethyl-17,18-dihydrorapamycin/AT replacements in extender modules 7 & 10; ER domain inserted in extender module 10

17,23-didesmethyl-19,20-dihydrorapamycin/AT replacements in extender modules 7 & 10; ER domain inserted in extender module 9

17,23-didesmethyl-21,22-dihydrorapamycin/AT replacements in extender modules 7 & 10; ER domain inserted in extender module 8

17,23-didesmethyl-17,18,19,20-tetrahydrorapamycin/AT replacements in extender modules 7 & 10; ER domain inserted in extender modules 9 & 10

17,23-didesmethyl-17,18,21,22-tetrahydrorapamycin/AT replacements in extender modules 7 & 10; ER domain inserted in extender modules 8 & 10

17,23-didesmethyl-19,20,21,22-tetrahydrorapamycin/AT replacements in extender modules 7 & 10; ER domain inserted in extender modules 8 & 9

17,23-didesmethyl-17,18,19,20,21,22-hexahydrorapamycin/AT replacements in extender modules 7 & 10; ER domain inserted in extender modules 8, 9 & 10

19-methylrapamycin/AT replacement in extender module 9 with the AT domain of DEBS extender module 2 or DEBS extender module 6

19,20-del-rapamycin/Deletion of extender module 9

18-hydroxyrapamycin/Deletion of DH domain of extender module 10

18-ketorapamycin/Deletion of KR and DH domains of extender module 10

18-saturated-rapamycin/Replacement of DH and KR domain of extender module 10 with KR, DH, and ER domains of DEBS extender module 4

Recombinant methods for manipulating modular PKS genes to make hybrid PKS enzymes are described in U.S. Pat. Nos. 5,672,491; 5,843,718; 5,830,750; and 5,712,146; and in PCT publication Nos. 98/49315 and 97/02358, ran each of which is incorporated herein by reference. A number of genetic engineering strategies have been used with DEBS to demonstrate that the structures of polyketides can be manipulated to produce novel natural products, primarily analogs of the erythromycins (see the patent publications referenced supra and Hutchinson, 1998, *Curr Opin Microbiol.* 1:319–329, and Baltz, 1998, *Trends Microbiol.* 6:76–83, incorporated herein by reference). These methods can be readily applied to the recombinant rapamycin PKS genes of the invention.

These techniques include: (i) deletion or insertion of modules to control chain length, (ii) inactivation of reduction/dehydration domains to bypass beta-carbon processing steps, (iii) substitution of AT domains to alter starter and extender units, (iv) addition of reduction/dehydration domains to introduce catalytic activities, and (v) substitution of ketoreductase KR domains to control hydroxyl stereochemistry. In addition, engineered blocked mutants of DEBS have been used for precursor directed biosynthesis of analogs that incorporate synthetically derived starter units. For example, more than 100 novel polyketides were produced by engineering single and combinatorial changes in multiple modules of DEBS. Hybrid PKS enzymes based on DEBS with up to three catalytic domain substitutions were constructed by cassette mutagenesis, in which various DEBS domains were replaced with domains from the rapamycin PKS (see Schweke et al., 1995, *Proc. Nat. Acad. Sci. USA* 92, 7839–7843, incorporated herein by reference) or one more of the DEBS KR domains was deleted. Functional single domain replacements or deletions were combined to generate DEBS enzymes with double and triple catalytic domain substitutions (see McDaniel et al., 1999, *Proc. Nat. Acad. Sci. USA* 96, 1846–1851, incorporated herein by reference).

Methods for generating libraries of polyketides have been greatly improved by cloning PKS genes as a set of three or more mutually selectable plasmids, each carrying a different wild-type or mutant PKS gene, then introducing all possible combinations of the plasmids with wild-type, mutant, and hybrid PKS coding sequences into the same host (see PCT Pub. No. 98/27203 and PCT app. No. US00/10021, each of which is incorporated herein by reference). This method can also incorporate the use of a KS1° mutant, which by mutational biosynthesis can produce polyketides made from diketide starter units (see Jacobsen et al., 1997, *Science* 277, 367–369, incorporated herein by reference), as well as the use of a truncated gene that leads to 12-membered macrolides or an elongated gene that leads to 16-membered ketolides. Moreover, by utlizing in addition one or more vectors that encode polyketide modification enzyme genes, a large collection of modified polyketides can be prepared.

The following Table lists references describing illustrative PKS genes and corresponding enzymes that can be utilized in the construction of the recombinant hybrid PKSs and the corresponding DNA compounds that encode them of the invention. Also presented are various references describing tailoring enzymes and corresponding genes that can be employed in accordance with the methods of the invention.

Avermectin
U.S. Pat. No. 5,252,474 to Merck.
MacNeil et al., 1993, *Industrial Microorganisms: Basic and Applied Molecular Genetics*, Baltz, Hegeman, & Skatrud, eds. (ASM), pp. 245–256, A Comparison of the Genes Encoding the Polyketide Synthases for Avermectin, Erythromycin, and Nemadectin.
MacNeil et al., 1992, *Gene* 115: 119–125, Complex Organization of the *Streptomyces avermitilis* genes encoding the avermectin polyketide synthase.

Candicidin (FR008)
Hu et al., 1994, *Mol. Microbiol.* 14: 163–172.

Epothilone
PCT Pub. No. 00/031247 to Kosan

Erythromycin
PCT Pub. No. 93/13663 to Abbott.
US Pat. No. 5,824,513 to Abbott.
Donadio et al., 1991, *Science* 252:675–9.
Cortes et al., Nov. 8, 1990, *Nature* 348:176–8, An unusually large multifunctional polypeptide in the erythromycin producing polyketide synthase of *Saccharopolyspora erythraea*.
Glycosylation Enzymes
PCT Pat. App. Pub. No. 97/23630 to Abbott.

FK-506
Motamedi et al., 1998, The biosynthetic gene cluster for the macrolactone ring of the immunosuppressant FK506, *Eur. J. Biochem.* 256: 528–534.
Motamedi et al., 1997, Structural organization of a multifunctional polyketide synthase involved in the biosynthesis of the macrolide immunosuppressant FK506, *Eur. J. Biochem.* 244: 74–80.
Methyltransferase
U.S. Pat. No. 5,264,355, issued Nov. 23, 1993, Methylating enzyme from Streptomyces MA6858. 31-O-desmethyl-FK506 methyltransferase.
Motamedi et al., 1996, Characterization of methyltransferase and hydroxylase genes involved in the biosynthesis of the immunosuppressants FK506 and FK520, *J. Bacteriol.* 178: 5243–5248.

FK-520
PCT Pub. No. 00/020601 to Kosan.
See also Nielsen et al., 1991, *Biochem.* 30:5789–96 (enzymology of pipecolate incorporation).

Lovastatin
U.S. Pat. No. 5,744,350 to Merck.

Narbomycin (and Picromycin)
PCT Pub. No. 99/61599 to Kosan.

Nemadectin
MacNeil et al., 1993, supra.

Niddamycin
Kakavas et al., 1997, Identification and characterization of the niddamycin polyketide synthase genes from *Streptomyces caelestis*, *J. Bacteriol.* 179: 7515–7522.

Oleandomycin
Swan et al., 1994, Characterisation of a Streptomyces antibioticus gene encoding a type I polyketide synthase which has an unusual coding sequence, *Mol. Gen. Genet.* 242: 358–362.
PCT Pub. No. 00/026349 to Kosan.
Olano et al., 1998, Analysis of a *Streptomyces antibioticus* chromosomal region involved in oleandomycin biosynthesis, which encodes two glycosyltransferases responsible for glycosylation of the macrolactone ring, *Mol. Gen. Genet.* 259(3): 299–308.

Platenolide
EP Pat. App. Pub. No. 791,656 to Lilly.

Rapamycin
Schwecke et al., August 1995, The biosynthetic gene cluster for the polyketide rapamycin, *Proc. Natl. Acad. Sci. USA* 92:7839–7843.
Aparicio et al., 1996, Organization of the biosynthetic gene cluster for rapamycin in *Streptomyces hygroscopicus*: analysis of the enzymatic domains in the modular polyketide synthase, *Gene* 169: 9–16.

Rifamycin
August et al., Feb. 13, 1998, Biosynthesis of the ansamycin antibiotic rifamycin: deductions from the molecular analysis of the rif biosynthetic gene cluster of *Amycolatopsis mediterranei* S669, *Chemistry & Biology*, 5(2): 69–79.

Soraphen
U.S. Pat. No. 5,716,849 to Novartis.
Schupp et al., 1995, *J. Bacteriology* 177: 3673–3679. A *Sorangium cellulosum* (Myxobacterium) Gene Cluster for the Biosynthesis of the Macrolide Antibiotic Soraphen A: Cloning, Characterization, and Homology to Polyketide Synthase Genes from Actinomycetes.

Spiramycin
U.S. Pat. No. 5,098,837 to Lilly.
Activator Gene
U.S. Pat. No. 5,514,544 to Lilly.

Tylosin
EP Pub. No. 791,655 to Lilly.
Kuhstoss et al., 1996, *Gene* 183:231–6, Production of a novel polyketide through the construction of a hybrid polyketide synthase.

U.S. Pat. No. 5,876,991 to Lilly.

Tailoring enzymes

Merson-Davies and Cundliffe, 1994, *Mol. Microbiol.* 13: 349–355. Analysis of five tylosin biosynthetic genes from the tylBA region of the *Streptomyces fradiae* genome.

As the above Table illustrates, there are a wide variety of PKS genes that serve as readily available sources of DNA and sequence information for use in constructing the hybrid PKS-encoding DNA compounds of the invention.

In constructing hybrid PKSs of the invention, certain general methods may be helpful. For example, it is often beneficial to retain the framework of the module to be altered to make the hybrid PKS. Thus, if one desires to add DH and ER functionalities to a module, it is often preferred to replace the KR domain of the original module with a KR, DH, and ER domain-containing segment from another module, instead of merely inserting DH and ER domains. One can alter the stereochemical specificity of a module by replacement of the KS domain with a KS domain from a module that specifies a different stereochemistry. See Lau et al., 1999, "Dissecting the role of acyltransferase domains of modular polyketide synthases in the choice and stereochemical fate of extender units" *Biochemistry* 38(5):1643–1651, incorporated herein by reference. One can alter the specificity of an AT domain by changing only a small segment of the domain. See Lau et al., supra. One can also take advantage of known linker regions in PKS proteins to link modules from two different PKSs to create a hybrid PKS. See Gokhale et al., Apr. 16, 1999, Dissecting and Exploiting Intermodular Communication in Polyketide Synthases", *Science* 284: 482–485, incorporated herein by reference.

The hybrid PKS-encoding DNA compounds of the invention can be and often are hybrids of more than two PKS genes. Even where only two genes are used, there are often two or more modules in the hybrid gene in which all or part of the module is derived from a second (or third) PKS gene.

The invention also provides libraries of PKS genes, PKS proteins, and ultimately, of polyketides, that are constructed by generating modifications in the rapamycin PKS so that the protein complexes produced have altered activities in one or more respects and thus produce polyketides other than the natural product of the PKS. Novel polyketides may thus be prepared, or polyketides in general prepared more readily, using this method. By providing a large number of different genes or gene clusters derived from a naturally occurring PKS gene cluster, each of which has been modified in a different way from the native cluster, an effectively combinatorial library of polyketides can be produced as a result of the multiple variations in these activities. As will be further described below, the metes and bounds of this embodiment of the invention can be described on the polyketide, protein, and the encoding nucleotide sequence levels.

As described above, a modular PKS "derived from" the rapamycin or other naturally occurring PKS includes a modular PKS (or its corresponding encoding gene(s)) that retains the scaffolding of the utilized portion of the naturally occurring gene. Not all modules need be included in the constructs; however, the constructs can also comprise more than 14 extender modules. On the constant scaffold, at least one enzymatic activity is mutated, deleted, replaced, or inserted so as to alter the activity of the resulting PKS relative to the original (native) PKS. Alteration results when these activities are deleted or are replaced by a different version of the activity, or simply mutated in such a way that a polyketide other than the natural product results from these collective activities. This occurs because there has been a resulting alteration of the starter unit and/or extender unit, stereochemistry, chain length or cyclization, and/or reductive or dehydration cycle outcome at a corresponding position in the product polyketide. Where a deleted activity is replaced, the origin of the replacement activity may come from a corresponding activity in a different naturally occurring PKS or from a different region of the rapamycin PKS. Any or all of the rapamycin PKS genes may be included in the derivative or portions of any of these may be included, but the scaffolding of a functional PKS protein is retained in whatever derivative is constructed.

Thus, a PKS derived from the rapamycin PKS includes a PKS that contains the scaffolding of all or a portion of the rapamycin PKS. The derived PKS also contains at least two extender modules that are functional, preferably three extender modules, and more preferably four or more extender modules, and most preferably 14 extender modules. The derived PKS also contains mutations, deletions, insertions, or replacements of one or more of the activities of the functional modules of the rapamycin PKS so that the nature of the resulting polyketide is altered at both the protein and DNA sequence levels. Particular preferred embodiments include those wherein a KS, AT, or ACP domain has been deleted or replaced by a version of the activity from a different PKS or from another location within the same PKS. Also preferred are derivatives where at least one non-condensation cycle enzymatic activity (KR, DH, or ER) has been deleted or added or wherein any of these activities has been mutated so as to change the structure of the polyketide synthesized by the PKS.

Thus, there are at least five degrees of freedom for constructing a hybrid PKS in terms of the polyketide that will be produced. First, the polyketide chain length is determined by the number of extender modules in the PKS, and the present invention includes hybrid PKSs that contain 14, as wells as fewer or more than 14, extender modules. Second, the nature of the carbon skeleton of the PKS is determined by the specificities of the acyl transferases that determine the nature of the extender units at each position, e.g., malonyl, methylmalonyl, ethylmalonyl, or other substituted malonyl. Third, the loading module specificity also has an effect on the resulting carbon skeleton of the polyketide. The loading module may use a different starter unit. As noted above, another method for varying loading module specificity involves inactivating the KS activity in extender module 1 (KS1) and providing alternative substrates that are chemically synthesized analogs of extender module 1 products, for extender module 2. This approach was illustrated in PCT publication Nos. 97/02358 and 99/03986, incorporated herein by reference, wherein the KS1 activity was inactivated through mutation. Fourth, the oxidation state at various positions of the polyketide will be determined by the dehydratase and reductase portions of the modules. This will determine the presence and location of ketone and alcohol moieties and C—C double bonds or C—C single bonds in the polyketide. Finally, the stereochemistry of the resulting polyketide is a function of three aspects of the synthase. The first aspect is related to the AT/KS specificity associated with substituted malonyls as extender units, which affects stereochemistry only when the reductive cycle is missing or when it contains only a ketoreductase, as the dehydratase would abolish chirality. Second, the specificity of the ketoreductase may determine the chirality of any beta-OH. Finally, the enoylreductase specificity for substituted malonyls as extender units may influence the stereochemistry when there is a complete KR/DH/ER available.

Thus, the modular PKS systems generally and the rapamycin PKS system particularly permit a wide range of polyketides to be synthesized. As compared to the aromatic PKS systems, the modular PKS systems accept a wider range of starter units, including aliphatic monomers (acetyl, propionyl, butyryl, isovaleryl, etc.), aromatics (aminohydroxybenzoyl), alicyclics (cyclohexanoyl), and heterocyclics (thiazolyl). Certain modular PKSs have relaxed specificity for their starter units (Kao et al., 1994, Science, supra). Modular PKSs also exhibit considerable variety with regard to the choice of extender units in each condensation cycle. The degree of beta-ketoreduction following a condensation reaction can be altered by genetic manipulation (Donadio et al., 1991, Science, supra; Donadio et al., 1993, Proc. Natl. Acad. Sci. USA 90: 7119–7123). Likewise, the size of the polyketide product can be varied by designing mutants with the appropriate number of modules (Kao et al., 1994, J. Am. Chem. Soc. 116:11612–11613). Lastly, modular PKS enzymes are particularly well known for generating an impressive range of asymmetric centers in their products in a highly controlled manner. The polyketides, antibiotics, and other compounds produced by the methods of the invention are typically single stereoisomeric forms. Although the compounds of the invention can occur as mixtures of stereoisomers, it may be beneficial in some instances to generate individual stereoisomers. Thus, the combinatorial potential within modular PKS pathways based on any naturally occurring modular, such as the rapamycin, PKS scaffold is virtually unlimited.

While hybrid PKSs are most often produced by "mixing and matching" portions of PKS coding sequences, mutations in DNA encoding a PKS can also be used to introduce, alter, or delete an activity in the encoded polypeptide. Mutations can be made to the native sequences using conventional techniques. The substrates for mutation can be an entire cluster of genes or only one or two of them; the substrate for mutation may also be portions of one or more of these genes. Techniques for mutation include preparing synthetic oligonucleotides including the mutations and inserting the mutated sequence into the gene encoding a PKS subunit using restriction endonuclease digestion. See, e.g., Kunkel, 1985, Proc. Natl. Acad. Sci. USA 82: 448; Geisselsoder et al., 1987, BioTechniques 5:786. Alternatively, the mutations can be effected using a mismatched primer (generally 10–20 nucleotides in length) that hybridizes to the native nucleotide sequence, at a temperature below the melting temperature of the mismatched duplex. The primer can be made specific by keeping primer length and base composition within relatively narrow limits and by keeping the mutant base centrally located. See Zoller and Smith, 1983, Methods Enzymol. 100:468. Primer extension is effected using DNA polymerase, the product cloned, and clones containing the mutated DNA, derived by segregation of the primer extended strand, selected. Identification can be accomplished using the mutant primer as a hybridization probe. The technique is also applicable for generating multiple point mutations. See, e.g., Dalbie-McFarland et al., 1982, Proc. Natl. Acad. Sci. USA 79: 6409. PCR mutagenesis can also be used to effect the desired mutations.

Random mutagenesis of selected portions of the nucleotide sequences encoding enzymatic activities can also be accomplished by several different techniques known in the art, e.g., by inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants, or by damaging plasmid DNA in vitro with chemicals. Chemical mutagens include, for example, sodium bisulfite, nitrous acid, nitrosoguanidine, hydroxylamine, agents which damage or remove bases thereby preventing normal base-pairing such as hydrazine or formic acid, analogs of nucleotide precursors such as 5-bromouracil, 2-aminopurine, or acridine intercalating agents such as proflavine, acriflavine, quinacrine, and the like. Generally, plasmid DNA or DNA fragments are treated with chemical mutagens, transformed into E. coli and propagated as a pool or library of mutant plasmids.

In constructing a hybrid PKS of the invention, regions encoding enzymatic activity, i.e., regions encoding corresponding activities from different PKS synthases or from different locations in the same PKS, can be recovered, for example, using PCR techniques with appropriate primers. By "corresponding" activity encoding regions is meant those regions encoding the same general type of activity. For example, a KR activity encoded at one location of a gene cluster "corresponds" to a KR encoding activity in another location in the gene cluster or in a different gene cluster. Similarly, a complete reductase cycle could be considered corresponding. For example, KR/DH/ER can correspond to a KR alone.

If replacement of a particular target region in a host PKS is to be made, this replacement can be conducted in vitro using suitable restriction enzymes. The replacement can also be effected in vivo using recombinant techniques involving homologous sequences framing the replacement gene in a donor plasmid and a receptor region in a recipient plasmid. Such systems, advantageously involving plasmids of differing temperature sensitivities are described, for example, in PCT publication No. WO 96/40968, incorporated herein by reference. The vectors used to perform the various operations to replace the enzymatic activity in the host PKS genes or to support mutations in these regions of the host PKS genes can be chosen to contain control sequences operably linked to the resulting coding sequences in a manner such that expression of the coding sequences can be effected in an appropriate host.

However, simple cloning vectors may be used as well. If the cloning vectors employed to obtain PKS genes encoding derived PKS lack control sequences for expression operably linked to the encoding nucleotide sequences, the nucleotide sequences are inserted into appropriate expression vectors. This need not be done individually, but a pool of isolated encoding nucleotide sequences can be inserted into expression vectors, the resulting vectors transformed or transfected into host cells, and the resulting cells plated out into individual colonies. The invention provides a variety of recombinant DNA compounds in which the various coding sequences for the domains and modules of the rapamycin PKS are flanked by non-naturally occurring restriction enzyme recognition sites.

The various PKS nucleotide sequences can be cloned into one or more recombinant vectors as individual cassettes, with separate control elements, or under the control of, e.g., a single promoter. The PKS subunit encoding regions can include flanking restriction sites to allow for the easy deletion and insertion of other PKS subunit encoding sequences so that hybrid PKSs can be generated. The design of such unique restriction sites is known to those of skill in the art and can be accomplished using the techniques described above, such as site-directed mutagenesis and PCR.

The expression vectors containing nucleotide sequences encoding a variety of PKS enzymes for the production of different polyketides are then transformed into the appropriate host cells to construct the library. In one straightforward approach, a mixture of such vectors is transformed into the selected host cells and the resulting cells plated into individual colonies and selected to identify successful transformants. Each individual colony has the ability to produce a particular PKS synthase and ultimately a particular polyketide. Typically, there will be duplications in some, most, or all of the colonies; the subset of the transformed colonies that contains a different PKS in each member colony can be considered the library. Alternatively, the expression vectors can be used individually to transform hosts, which transformed hosts are then assembled into a library. A variety of strategies are available to obtain a multiplicity of colonies each containing a PKS gene cluster derived from the naturally occurring host gene cluster so that each colony in the library produces a different PKS and ultimately a different polyketide. The number of different polyketides that are produced by the library is typically at least four, more typically at least ten, and preferably at least 20, and more preferably at least 50, reflecting similar numbers of different altered PKS gene clusters and PKS gene products. The number of members in the library is arbitrarily chosen; however, the degrees of freedom outlined above with respect to the variation of starter, extender units, stereochemistry, oxidation state, and chain length enables the production of quite large libraries.

Methods for introducing the recombinant vectors of the invention into suitable hosts are known to those of skill in the art and typically include the use of $CaCl_2$ or agents such as other divalent cations, lipofection, DMSO, protoplast transformation, infection, transfection, and electroporation. The polyketide producing colonies can be identified and isolated using known techniques and the produced polyketides further characterized. The polyketides produced by these colonies can be used collectively in a panel to represent a library or may be assessed individually for activity.

The libraries of the invention can thus be considered at four levels: (1) a multiplicity of colonies each with a different PKS encoding sequence; (2) the proteins produced from the coding sequences; (3) the polyketides produced from the proteins assembled into a function PKS; and (4) antibiotics or compounds with other desired activities derived from the polyketides.

Colonies in the library are induced to produce the relevant synthases and thus to produce the relevant polyketides to obtain a library of polyketides. The polyketides secreted into the media can be screened for binding to desired targets, such as receptors, signaling proteins, and the like. The supernatants per se can be used for screening, or partial or complete purification of the polyketides can first be effected. Typically, such screening methods involve detecting the binding of each member of the library to receptor or other target ligand. Binding can be detected either directly or through a competition assay. Means to screen such libraries for binding are well known in the art. Alternatively, individual polyketide members of the library can be tested against a desired target. In this event, screens wherein the biological response of the target is measured can more readily be included. Antibiotic activity can be verified using typical screening assays such as those set forth in Lehrer et al., 1991, *J. Immunol. Meth*. 137:167–173, incorporated herein by reference.

The invention provides methods for the preparation of a large number of polyketides. These polyketides are useful compounds directly and as intermediates in formation of compounds with antifungal, antitumor, and immunosuppressant activity. The methods and recombinant host cells of the invention are useful in the production of polyketides. The compounds of the invention can be produced by growing and fermenting the host cells of the invention under conditions known in the art for the production of other polyketides. The compounds of the invention can be isolated from the fermentation broths of these cultured cells and purified by standard procedures.

The compounds can be readily formulated to provide the pharmaceutical compositions of the invention. The pharmaceutical compositions of the invention can be used in the form of a pharmaceutical preparation, for example, in solid, semisolid, or liquid form. This preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, solutions, emulsions, suspensions, and any other form suitable for use.

The carriers which can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used. For example, the compounds of the invention may be utilized with hydroxypropyl methylcellulose essentially as described in U.S. Pat. No. 4,916,138, incorporated herein by reference, or with a surfactant essentially as described in EPO patent publication No. 428,169, incorporated herein by reference.

Oral dosage forms may be prepared essentially as described by Hondo et al., 1987, *Transplantation Proceedings XIX*, Supp. 6: 17–22, incorporated herein by reference. Dosage forms for external application may be prepared essentially as described in EPO patent publication No. 423,714, incorporated herein by reference. The active compound is included in the pharmaceutical composition in an amount sufficient to produce the desired effect upon the disease process or condition.

For the treatment of conditions and diseases caused by infection, cancer, or autoimmune disorder or to achieve immunosuppression, a compound of the invention may be administered orally, topically, parenterally, by inhalation spray, or rectally in dosage unit formulations containing conventional non-toxic pharmaceutically acceptable carriers, adjuvant, and vehicles. The term parenteral, as used herein, includes subcutaneous injections, and intravenous, intramuscular, and intrasternal injection or infusion techniques.

Dosage levels of the compounds of the invention are of the order from about 0.01 mg to about 50 mg per kilogram of body weight per day, preferably from about 0.1 mg to about 10 mg per kilogram of body weight per day. The dosage levels are useful in the treatment of the above-indicated conditions (from about 0.7 mg to about 3.5 mg per patient per day, assuming a 70 kg patient). In addition, the compounds of the invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain from 0.5 mg to 5 gm of active agent compounded with an appropriate and convenient amount of carrier material, which may vary from about 5percent to about 95 percent of the total composition. Dosage unit forms will generally contain from about 0.5 mg to about 500 mg of active ingredient. For external administration, the compounds of the invention may be formulated within the range of, for example, 0.00001% to 60% by weight, preferably from 0.001% to 10% by weight, and most preferably from about 0.005% to 0.8% by weight.

It will be understood, however, that the specific dose level for any particlular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

A detailed description of the invention having been provided above, the following examples are given for the purpose of illustrating the invention and shall not be construed as being a limitation on the scope of the invention or claims.

EXAMPLE 1

General Methodology

Bacterial strains, plasmids, and culture conditions. *Streptomyces coelicolor* CH999 described in WO 95/08548, published Mar. 30, 1995, or *S. lividans* K4–114, described in Ziermann and Betlach, January 1999, Recombinant Polyketide Synthesis in Streptomyces: Engineering of Improved Host Strains, *BioTechniques* 26:106–110, incorporated herein by reference, was used as an expression host. DNA manipulations were performed in Escherichia coli XL1-Blue, available from Stratagene. *E. coli* MC1061 is also suitable for use as a host for plasmid manipulation. Plasmids were passaged through *E. coli* ET12567 (dam dcm hsdS $Cm^r$) (MacNeil, 1988, *J. Bacteriol.* 170: 5607, incorporated herein by reference) to generate unmethylated DNA prior to transformation of *S. coelicolor* or *Saccharopolyspora erythraea*. *E. coli* strains were grown under standard conditions. *S. coelicolor* strains were grown on R2YE agar plates (Hopwood et al., *Genetic manipulation of Streptomyces. A laboratory manual*. The John Innes Foundation: Norwich, 1985, incorporated herein by reference).

Many of the expression vectors of the invention illustrated in the examples are derived from plasmid pRM5, described in WO 95/08548, incorporated herein by reference. This plasmid includes a colEI replicon, an appropriately truncated SCP2*Streptomyces replicon, two act-promoters to allow for bidirectional cloning, the gene encoding the actII-ORF4 activator which induces transcription from act promoters during the transition from growth phase to stationary phase, and appropriate marker genes. Engineered restriction sites in the plasmid facilitate the combinatorial construction of PKS gene clusters starting from cassettes encoding individual domains of naturally occurring PKSs. When plasmid pRM5 is used for expression of a PKS, all relevant biosynthetic genes can be plasmid-borne and therefore amenable to facile manipulation and mutagenesis in *E. coli*. This plasmid is also suitable for use in Streptomyces host cells. Streptomyces is genetically and physiologically well-characterized and expresses the ancillary activities required for in vivo production of most polyketides. Plasmid pRM5 utilizes the act promoter for PKS gene expression, so polyketides are produced in a secondary metabolite-like manner, thereby alleviating the toxic effects of synthesizing potentially bioactive compounds in vivo.

Manipulation of DNA and organisms. Polymerase chain reaction (PCR) was performed using Pfu polymerase (Stratagene; Taq polymerase from Perkin Elmer Cetus can also be used) under conditions recommended by the enzyme manufacturer. Standard in vitro techniques were used for DNA manipulations (Sambrook et al. *Molecular Cloning: A Laboratory Manual* (Current Edition)). *E. coli* was transformed using standard calcium chloride-based methods; a Bio-Rad *E. coli* pulsing apparatus and protocols provided by Bio-Rad could also be used. *S. coelicolor* was transformed by standard procedures (Hopwood et al. *Genetic manipulation of Streptomyces. A laboratony manual*. The John Innes Foundation: Norwich, 1985), and depending on what selectable marker was employed, transformants were selected using 1 mL of a 1.5 mg/mL thiostrepton overlay, 1 mL of a 2 mg/mL apramycin overlay, or both.

EXAMPLE 2

Production of 16-Desmethyl-27-desmethoxyrapamycin

*Streptomyces hygroscopicus* ATCC 29253 was modified to delete the rapL, rapM, rapN, rapO, and rapQ genes by the following procedure. The recombinant host cell produced was designated *S. hygroscopicus* KOSO20-70 and produces 16-desmethyl-27-desmethoxyrapamycin. This compound has lower immunosuppressive activity than rapamycin but can has utility as an immunosuppressant, a neurotrophin, and as an antifungal agent. References cited in this example are incorporated herein by reference and are identified by a number in parentheses; the numbered listing of references is located at the end of this example.

Rapamycin (sirolimus, Rapamune™) is an immunosuppressant macrolide produced by *Streptomyces hygroscopicus* ATCC 29253. Originally discovered as an antifungal agent (16), it was later found to have immunosuppressive activity, preventing activated interleukin-2 receptors from transducing a proliferation signal, a mechanism distinct from that of the immunosuppressants cyclosporin or FK506 (2, 3). Rapamycin is a very complex molecule, making it difficult to synthesize many analogs that might have superior properties. However, rapamycin biosynthesis involves a modular polyketide synthase (PKS) system (15) that has been shown to be amenable to genetic engineering to obtain novel analogs (7).

Based on data from isotope labeling studies (13, 14), the product of the PKS complex and the subsequent modification reactions are known to be as shown below.

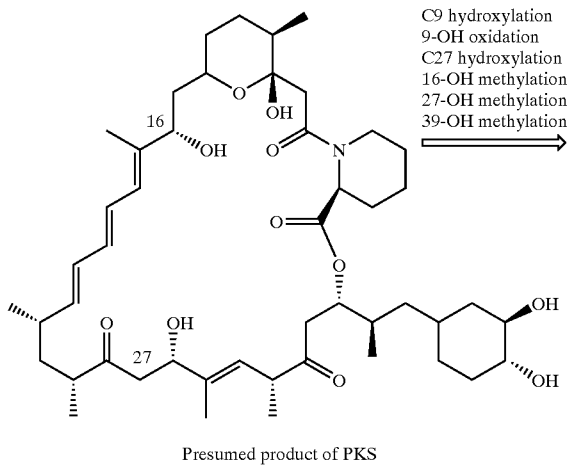

C9 hydroxylation
9-OH oxidation
C27 hydroxylation
16-OH methylation
27-OH methylation
39-OH methylation Presumed product of PKS

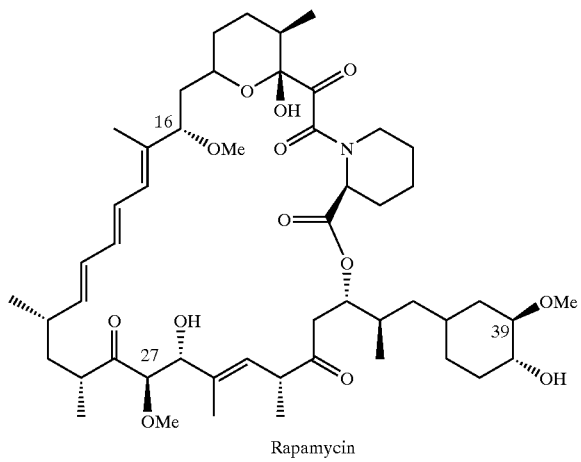

Rapamycin

The modification reactions are listed in an arbitrary order, except that the 9-hydroxylation must occur before the 9-hydroxyl oxidation. The temporal order of these reactions is not known and may not be constrained.

A large PKS complex first synthesizes the 31-member macrolactone precursor, which includes a shikimate-derived starter unit and pipecolate as the final unit incorporated by a non-ribosomal peptide synthetase. The precursor is hydroxylated at C-9 and C-27, the 16-, 27- and 31-hydroxyls are methylated, and the 9-hydroxyl is oxidized to form the alpha-ketoamide (13, 14). However, the order in which these post-PKS reactions occur is not known, nor has each reaction been assigned to a specific gene or genes.

Analysis of a 100 kb region of the S. hygroscopicus genome encompassing the rapamycin biosynthetic gene cluster (1, 11, 15) revealed five genes immediately downstream of rapC putatively encoding an O-methyltransferase (rapQ), a ferredoxin (rapO), a P450 hydroxylase (rapN), a second O-methyltransferase (rapM) and lysine cyclodeaminase (rapL). By introducing a frameshift mutation into rapL (8), this gene was recently proven to encode the activity needed to convert lysine into pipecolic acid, the final unit incorporated into the macrolactone precursor. A second P450 hydroxylase gene (rapJ) and a third O-methyltransferase gene (rapI) are closest in sequence to fkbD and fkbM, which hydroxylate C-9 and methylate the 31-hydroxyl of the dihydroxycyclohexane ring, respectively, of FK506 (12, 17). However, the regiospecificity of the two P450 hydroxylases and the three O-methyl transferases in the rapamycin cluster has not been previously assigned.

Figure 2:
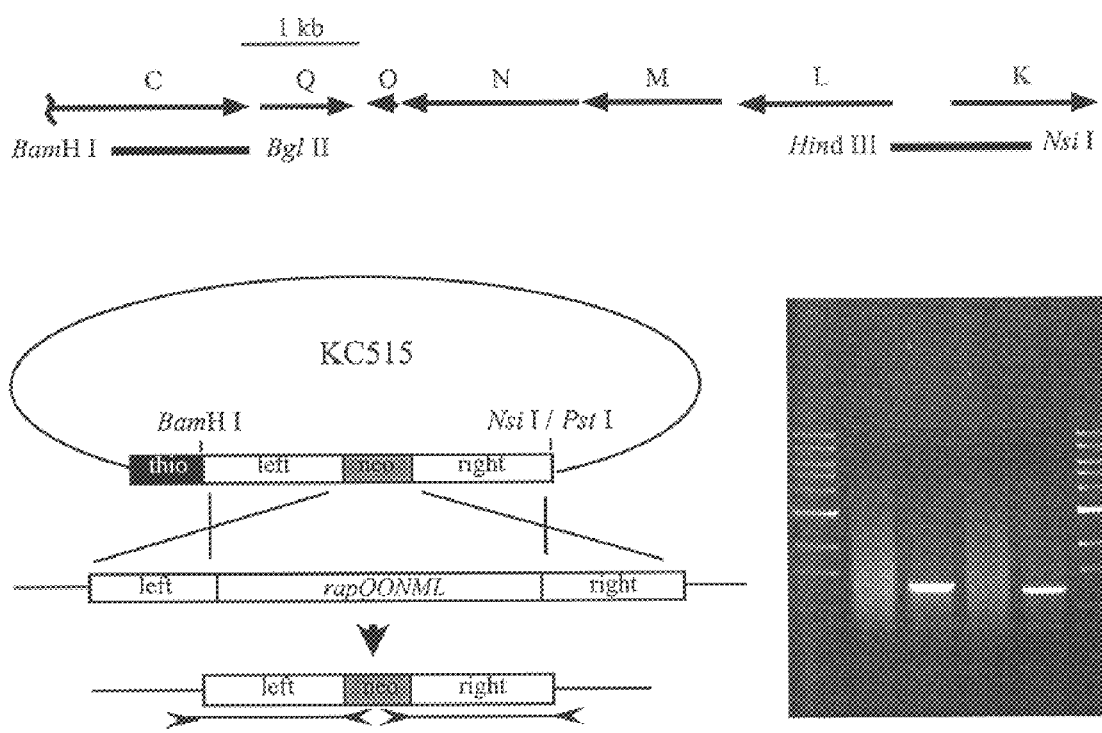
FIG. 2 shows the rapQONML region and the location of the two flanking sequences used in construction of recombinant phage KC515 (top); a diagram of the result of the double crossover event with the recombinant phage DNA (left bottom); and the results of the PCR reactions from wild-type and KOS20-001 strains (left right).

There remains a need for rapamycin analogues with improved activity and means for their production. The present invention meets such needs in that it provides, inter alia, a recombinant organism from which the five genes, rapQONML, have been replaced with a neomycin resistance marker and the compound 16-desmethyl-27-desmethoxyrapamycin, which cultures of this strain, when fed pipecolate, produce in significant amounts. The strain in which the rapQONML region was replaced with a neomycin resistance cassette was constructed as diagrammed in FIG. 2. As shown in FIG. 2, sequences flanking the rapQONML region were cloned by PCR, the Tn5 neomycin resistance cassette of pFDNEO-S was inserted between them, and the cassette was ligated into the KC515 phage vector. The recombinant phage was used to obtain NeoR lysogens of S. hygroscopicus, which were screened for the double crossover event by patching to agar medium containing both neomycin and thiostrepton. NeoR, ThioS strains were analyzed by PCR to confirm the presence of both amplimers spanning the homologous sequences. DNA from strain KOS20-001 gave both amplimers, indicating that the rapQONML genes had been replaced with the neo marker. Thus, in the above diagram, the rapQONML region and the location of the two flanking sequences used in the construction are shown. Also shown is the result of the double crossover event with the recombinant phage DNA; the location of the two amplimers used to verify the double crossover strain is indicated by lines between convergent arrows representing the primers. Finally, the results of the PCR reactions with DNA from wild type (lanes 1 & 3) and KOS20-001 (lanes 2 & 4) are shown. The primers amplified the left region (lanes 1 & 2) or the right region (lanes 3 & 4). The marker lanes (M) are New England Biolabs 1 kb ladder.

The engineered (KOS20-001) and wild-type (ATCC 29253) strains were fermented in the presence and absence of 1 mg/L D,L-pipecolate, and the cultures were analyzed as described below. HPLC-MS showed that the deletion strain, when grown in the presence of pipecolate, produced no detectable rapamycin, but instead produced a new metabolite also with a strong absorption at 287 nm. Comparison of the mass spectrum of rapamycin with that of the new metabolite showed fragmentation that was consistent with it being 16-desmethyl-27-desmethoxyrapamycin, as shown in Table 1, below.

TABLE 1

Comparsion of fragment masses observed in the LC-MS for 16-desmethyl-27-desmethoxyrapamycin and authentic rapamycin.

| 16-desmethyl-27-desmethoxyrapamycin | calculated | observed | rapamycin | calculated | observed |
|---|---|---|---|---|---|
| $C_{49}H_{76}NO_{12}$ $(M + H)^+$ | 870.5368 | none | $C_{51}H_{80}NP_{13}$ $(M + H)^+$ | 914.5630 | none |
| $C_{49}H_{74}NO_{11}$ $(M + H—H_2O)^+$ | 852.5262 | 852.5256 | $C_{50}H_{74}NO_{12}$ $(M + H—CH_3OH)^+$ | 882.5368 | 883 |
| $C_{49}R_{72}NO_{10}$ $(M + H-2H_2O)$ | 834.5156 | 834.523 | $C_{50}H_{74}NO_{11}$ $(M + H—H_2O—CH_3OH)^+$ | 864.5262 | 865 |
| $C_{49}H_{70}NO_9$ $(M + H-3H_2O)^+$ | 816.5051 | 816.511 | $C_{50}H_{72}NO_{10}$ $(M + H—CH_3OH-2H_2O)^+$ | 846.5156 | 847 |
| $C_{49}H_{70}NO_9$ $(M + H-4H_2O)^+$ | 798.4945 | 798.511 | $C_{49}H_{68}NO_9$ $(M + H-2CH_{30}H-2H_2O)^+$ | 814.4894 | 815 |
| $C_{30}H_{42}NO_6$ Frag. X | 512.3012 | 512.3007 | | | |
| $C_{19}H_{31}O_2$ Frag. Y | 323.2222 | 323 | $C_{19}H_{31}O_2$ Frag. Y | 323.2222 | 323 |
| $C_{19}H_{29}O_3$ Frag. Y—$H_2O$ | 305.2117 | 305.2111 | $C_{19}H_{29}O_3$ Frag. Y—$H_2O$ | 305.2117 | 305 |
| $C_{18}H_{25}O_2$ Frag. Y—$H_2O$—MeOH | 273.1855 | 273 | $C_{18}H_{25}O_2$ Frag. Y—$H_2O$—MeOH | 273.1855 | 273 |

By analogy to the series of losses of 2MeOHs and 2H$_2$Os observed for rapamycin, the mass spectra of 16-desmethyl-27-desmethoxyrapamycin showed sequential loss of 4H$_2$Os. Both compounds displayed loss of fragment Y, shown below, and fragments derived from it, indicating that this portion of the molecule had not been changed. Fragment masses observed for rapamycin and the analog are listed in Table 1, above.

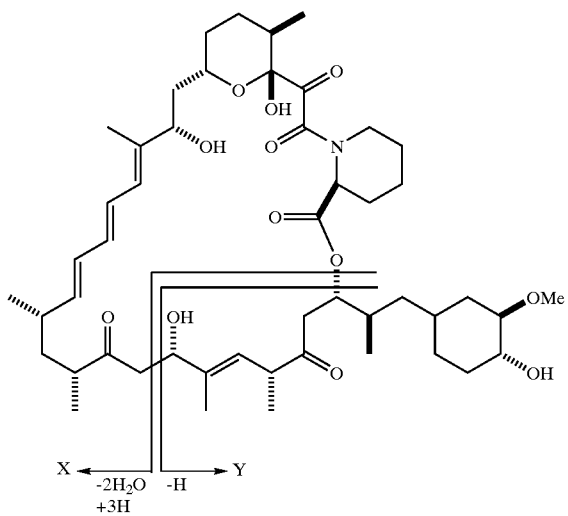

Fragment X, shown above, also supports the proposed structure. KOS20-001 was cultured in a 10-liter fermenter to provide enough material for further characterization. 16-Desmethyl-27-desmethoxyrapamycin was isolated from the fermentation broth as described below. Partial NMR assignments were made from a series of 1D and TOCSY, HSQC, and HMBC experiments, as shown in Table 2.

TABLE 2

Selected NMR data for 16-desmethyl-27-desmethoxyrapamycin and rapamycin.[a]

| Position | 16-desmethyl-27-desmethoxyrapamycin $^1H$ δ (ppm) | $^{13}C$ δ (ppm) | rapamycin[b] $^1H$ δ (ppm) | $^{13}C$ δ (ppm) |
|---|---|---|---|---|
| 1 | | 170.4 | | 169.2 |
| 2 | 5.20 | 51.8 | 5.29 | 51.3 |
| 8 | | 166.6 | | 166.8 |
| 9 | | 194.8 | | 192.5 |
| 10 | | 98.9 | | 98.5 |
| 27 | 2.52 (dd, 17.5, 3.0 Hz) 2.64 (dd, 17.5, 9.0 Hz) | 46.8 | 3.71 | 84.9 |
| 32 | | 208.7 | | 208.2 |
| 39 | 2.93 | 84.4 | 2.93 | 84.4 |
| 40 | 3.39 | 73.9 | 3.35 | 73.9 |
| 27-OMe | | | 3.34 | 59.5 |
| 39-OMe | 3.41 | 56.4 | 3.41 | 56.5 |

[a]Data reported is for the major conformer in CDCl$_3$.
[b]Data from reference 1.

As anticipated, the $^1$H NMR spectrum of 16-desmethyl-27-dsmethoxyrapamycin displayed only one major methoxy group signal at δ 3.41 and the HSQC data showed that these protons were attached to a carbon resonating at 56.4. An HMBC cross peak connected the methoxy function to a carbon with a signal at δ 84.4 (C-39). A TOCSY correlation was observed between H-39 (2.93) and a signal at δ 3.38 (H40), which provided further proof of the location of the methoxy group. These values are in good agreement with those reported for rapamycin (10).

Evidence that the new metabolite differed from rapamycin at the 27-position was provided by the $^1$H NMR spectrum. The region of δ 3.65–3.75, where H-27 of rapamycin resonates, was devoid of any signals, and two sets of unique signals at δ 2.63 (dd, 17.5, 9.5 Hz) and 2.47 (dd, 17.5, 3.0 Hz), similar to those previously reported for for H2–27 of 27-desmethoxyrapamycin (5), were observed. In combination, the data indicates that the deletion strain produces the new metabolite 16-desmethyl-27-desmethoxyrapamycin.

Because the alpha-keto amide and 39-methoxy functions are present on the rapamycin analog, the rapQONML genes are not involved in these reactions. The remaining methyltransferase gene in the rapQONML deletion strain, rapI, therefore must encode the enzyme responsible for methylating the 39-hydroxyl on a rapamycin precursor, consistent with the observation that rapI is most closely related to fkbM in the FK506 cluster. A functional fkbM gene has been shown to be required for methylation of the 31-hydroxyl of an FK506 precursor. Therefore, the methyltransferases encoded by the rapQ and rapM genes must be responsible for methylation of the 16- and 27-hydroxyls, although the precise specificity of these enzymes cannot be defined from the result. The remaining P450 hydroxylase gene in the rapamycin cluster of the rapQONML deletion strain is rapJ which therefore must encode the enzyme for hydroxylation of carbon 9, consistent with its close homology to fkbD. The rapN gene, therefore, must be responsible for the other hydroxylation at carbon 27.

Because significant levels of 16-demethyl-27-desmethoxyrapamycin were produced by the engineered strain, the other post-PKS processing reactions do not require a precursor that has already been modified at the 16 and 27 positions. Thus, either the 16 and 27 positions are the last to be modified, or the post-PKS modification enzymes recognize only a region of the molecule surrounding the target for modification.

The bacterial strains, plasmids and phages used are listed in Table 3, below.

TABLE 3

Bacterial strains, plasmids and phages

| Strain, plasmid or phage | Relevant characteristics | Reference or source |
|---|---|---|
| *E. coli* | | |
| XL1-Blue | common vector host | Stratagene |
| *S. hygroscopicus* | | |
| NRRL 5491 | wild-type rapamycin producer | ATCC |
| KOS20-001 | rapQONML deletion strain | This work |
| *S. lividans* | | |
| TK24 | host for phage propagation | 6 |
| Plasmids | | |
| Litmus 28 | general cloning vector | New, England Biolabs |
| pCR-Script | vector for PCR amplimers | Stratagene |
| pFDNEO-S | source of neoR marker | |
| PKOS7-150 | Litmus 28 with new polylinker | This work |
| pKOS20-55.2 | 5' flanking amplimer in pCR-Script | This work |
| pKOS20-56.1 | 3' flanking amplimer in pCR-Script | This work |
| pKOS20-61.1 | 3' flanking amplimer in pKOS7-150 | This work |
| pKOS20-68 | 5' flanking amplimer in pFDNEO-S | This work |
| pKOS20-70 | rapQONML::neo replacement cassette | This work |
| Phage | | |
| KC515 | c+ ΔattP::tsr,vph | 6 |
| phKOS20-001 | KC515 Δvph:: replacement cassette | This work |

Plasmid pFDNEO-S was a kind gift of Prof. Ryszard Brzezinski of the Université du Sherbrooke, Canada. *S. hygroscopicus* ATCC 29253 and recombinant strain KOS20-001 were plated on SY (1% soluble starch, 0.2% yeast extract, 20% agar) to obtain spores.

The cassette for replacement of rapQONML with a neomycin resistance gene was constructed as shown in above. Approximately 1.2 kb regions upstream and downstream of the rapQONML genes were obtained by PCR amplification from *S. hygroscopicus* genomic DNA. The location of each primer on the published rapamycin cluster sequence (1, 11, 15) given below refers to the 3' end of each primer. The upstream region was obtained with primers from nucleotide 89986

(5'-ATCGGATCCGC GCCAGGTCCGGCGACCCGTCCGCITCC-3') (SEQ ID NO: 1), introducing a BamHI site, and 91124

(5'-GATAGATCTAGACCGAAGGCCGACATCACGGT GTCGAAC-3') (SEQ ID NO: 2), introducing a BglII site. The downstream region was obtained with primers from 95072

(5'-ATCAAGCTTG CTTGATGTCACGCTGGCACAGAACCTTGG-3') (SEQ ID NO: 3), introducing a HindIII site, and 96218

(5'-GATATGCATCCGTGCCGTCCCAGGTTCTCGGCA CCGATC-3') (SEQ ID NO: 4), introducing an NsiI site. The PCR mixes included cloned Pfu polymerase (Stratagene), the manufacturer's buffer, 10% DMSO, 200 μM each of dATP, dTTP, dCTP, and 100 gM each of dGTP and deaza-dGTP (Roche). Thirty cycles of 30 sec at 95°, 30 sec at 60° and 3 min at 72° were used. Each amplimer was cloned into the SrfI site of pCR-Script (Stratagene) to give pKOS20-55.2 and pKOS20-56.1, respectively, and clones were verified by sequencing.

Plasmid pKOS7-150 was derived from Litmus 28 and has the following sequence between the SnaBI and AvrII sites: 5'-TGGATCCACAGATCTGCCTGC AGCATCTA-GAAAGCTT ACATGCATCCTAG-3' (SEQ ID NO: 5). The left region was isolated from pKOS20-56.1 as a 1.2 kb EcoRI-BglII fragment and cloned into the EcoRI-BamHI sites of pFDNEO-S (4), to give pKOS20-68. The right region was isolated from pKOS20-56.1 as a 1.2 kb HindIII-NsiI fragment and cloned into the same sites of pKOS7-150 to give pKOS20-61.1. The 2.2 kb BamHI-HindIII fragment of pKOS20-68 was moved into the same sites of pKOS20-61.1 to give pKOS20-70, in which the neomycin resistance gene was inserted between the rapQONML flanking sequences.

The cassette described above was isolated from pKOS20-70 as a 3.4 kb BamHI-NsiI fragment and ligated to the BamHI-PstI sites of KC515 DNA and the DNA transfected into *S. lividans* TK24 protoplasts as described (6). Recombinant phage plaques were identified using PCR. Phage harboring the replacement cassette was mixed with freshly germinated spores of ATCC 29253 and plated onto modified oatmeal agar ($10^7$–$10^8$ spores per plate; MOI of 5–10) as described (9). After 20 h at 30° C., plates were overlayed with neomycin (10 μg/ml final concentration) and incubated about 10 days. Selected colonies were transferred to minimal medium containing 20 μg/ml neomycin and those that grew well after about 10 days were streaked on minimal medium containing 20 μg/ml neomycin to obtain pure clones. Clones were tested for the double crossover event by patching to medium with neomycin alone and neomycin plus thiostrepton. Selected NeoR, ThioS strains were grown in Difco tryptic soy broth supplemented with 1% glucose, 100 mM MES (2-(N-morpholino)-ethane sulfonic acid) buffer, pH 6.0 and DNA was isolated as described (6). The DNA was analyzed by PCR for the presence of amplimers diagnostic of the double crossover replacement event. The primer pairs annealed to regions outside the left homologous sequence (5'-CGGGCGTCTGATCGACCAGGATGAGATGGG-3') (SEQ ID NO: 6) and within the neo cassette promoter (5'-TATGTTGGTGTCATTCTAACCAGAATCGGCAAAAGATGTCA-3') (SEQ ID NO: 7), or outside the right homologous sequence (5'-GCGAGGGCGTAGCCCCGGCG-3') (SEQ ID NO: 8) and in the polylinker at the 3' end of the neo cassette (5'-GTCGACCTGCAGGCATGCAAGCTT-3') (SEQ ID NO: 9). A strain in which the rapQONML region was correctly replaced by the neo cassette was designated KOS20-001.

Spores of *S. hygroscopicus* ATCC 29253 and KOS20-001 were inoculated into 40 ml of supplemented TSB (8) in 250 mL baffled flasks. After 20 hours, cultures were harvested, resuspended in 30% glycerol and dispensed into 1 ml aliquots to give a working cell bank. One frozen cell vial was used to inoculate 40 mL of supplemented TSB (8) in 250 ml baffled flasks. At about 20 hrs, the concentration of glucose approached zero, as measured with a YSI 2700 Select biochemistry analyzer, at which time D,L-pipecolate (Sigma) was added to the KOS70-001 cultures (1 mg/ml final concentration). Aliquots of the cultures were extracted after 3–4 days (when fully grown) as follows. To an aliquot of whole broth two volumes of acetone were added and the mixture was sonicated one minute on ice with a sonic dismembranator 60 (Fisher) set at maximum. Three volumes of ethyl acetate was added, relative to the original aliquot, and the mixture was shaken. After centrifugation, the upper ethyl acetate phase was transferred to a new container, dried by adding anhydrous sodium sulfate, and concentrated by rotary evaporation. The residue was redissolved in ethyl acetate for analysis (0.5% of the original broth volume).

Extracts were analyzed using a system comprised of a Beckman System Gold HPLC, an Alltech ELSD detector, and a PE SCIEX API100 LC MS-based detector equipped with an atmospheric pressure chemical ionization source. The eluent of a Metachem Inertsil ODS-3 column (5 µm, 4.6×150 mm) at 50° C. of a linear gradient from 50% to 100% MeCN (0.1% HOAc) at 1 mL/min over 5 min was monitored by UV at 287 nm, ELSD, and MS. Under these conditions, rapamycin eluted at 9.4 min and 16-desmethyl-27-desmethoxyrapamycin at 8.4 min. High resolution LC/MS of a purified sample of 16-desmethyl-27-desmethoxyrapamycin was obtained on a PE Biosystems Mariner API-TOF MS also configured with an atmospheric pressure chemical ionization source.

KOS20-001 was cultured in a 10-liter fermenter of supplemented TSB medium seeded with a 2-day old 500 mL culture of the same medium. At 3 days, the culture was harvested, an equal volume of methanol was added, and after 30 minutes the suspension was centrifuged. The supernatant was subjected to solid-phase extraction on HP-20 (500 ml column volume, 100 ml/min). After capture, the column was washed with 2 liters of MeOH-$H_2O$ (1:1), followed by 2 liters of MeOH-$H_2O$ (2:1). The new metabolite was then eluted from the column with 1.5 liters of MeOH. A 1-gram portion of the resulting 2.5 g of residue was fractionated over LH-20 ($CH_2Cl_2$-MeOH, 1:1). Fractions containing the analog were pooled and re-chromatographed over LH-20 (heptane-dichloromethane-ETOH, 10:10:1). Final purification was by HPLC (10×250 mm, Metachem Inertsil ODS-3, linear gradient from 50% MeCN—$H_2O$ to 95% MeCN—$H_2O$ over 30 min, 5 ml/min, UV=287 nm).

The following publications are incorporated herein by reference; in the foregoing text, these references are denoted by parenthetical reference to the number according to which the reference is listed below.

1. Aparicio et al. 1996. Organization of the biosynthetic gene cluster for rapamycin in *Streptomyces hygroscopicus*: analysis of the enzymatic domains in the modular polyketide synthase. Gene. 169(1):9–16.
2. Bierer, B. E. 1995. Mechanisms of action of immunosuppressive agents: cyclosporin A, FK506, and rapamycin. Proc Assoc Am Physicians. 107(1):2840.
3. Brazelton et al. 1996. Molecular mechanisms of action of new xenobiotic immunosuppressive drugs: tacrolimus (FK506), sirolimus (rapamycin), mycophenolate mofetil and leflunomide. Curr Opin Immunol. 8(5):710–20.
4. Denis et al. 1991. An improved aminoglycoside resistance gene cassette for use in gram-negative bacteria and Streptomyces. FEMS Microbiol Lett. 65(3):261–4.
5. Findlay et al. 1982. The structure of demethoxyrapamycin. Can. J. Chem. 60:2046–2047.
6. Hopwood et al. 1985. Genetic Manipulation of Streptomyces: A Laboratory Manual. The John Innes Foundation, Norwich, UK.
7. Katz, L. 1997. Manipulation of modular polyketide synthases. Chem. Rev. 97(7):2557–2576.
8. Khaw et al. 1998. Mutational biosynthesis of novel rapamycins by a strain of *Streptomyces hygroscopicus* NRRL 5491 disrupted in rapL, encoding a putative lysine cyclodeaminase. J Bacteriol. 180(4):809–14.
9. Lomovskaya et al. 1997. Gene disruption and replacement in the rapamycin-producing *Streptomyces hygroscopicus* strain ATCC 29253. Microbiology. 143(Pt 3):875–83.
10. McAlpine et al. 1991. Revised NMR assignments for rapamycin. J Antibiot (Tokyo). 44(6):688–90.
11. Molnar et al. 1996. Organisation of the biosynthetic gene cluster for rapamycin in *Streptomyces hygroscopicus*: analysis of genes flanking the polyketide synthase. Gene. 169(1):1–7.
12. Motamedi et al. 1996. Characterization of methyltransferase and hydroxylase genes involved in the biosynthesis of the immunosuppressants FK506 and FK520. J Bacteriol. 178(17):5243–8.
13. Paiva et al. 1991. Incorporation of acetate, propionate, and methionine into rapamycin by *Streptomyces hygroscopicus*. J Nat Prod. 54(1):167–77.
14. Reynolds et al. 1997. Rapamycin, FK506, and ascomycin-related compounds, p. 497–520. In W. R. Strohl (ed.), Biotechnology of Antibiotics, 2nd, rev. and expand ed, vol. 82. M. Dekker, New York.
15. Schwecke et al. 1995. The biosynthetic gene cluster for the polyketide immunosuppressant rapamycin. Proc Natl Acad Sci U S A. 92(17):783943.
16. Sehgal et al. 1975. Rapamycin (AY-22,989), a new antifungal antibiotic. II. Fermentation, isolation and characterization. J Antibiot (Tokyo). 28(10):727–32.
17. Shafiee et al. 1997. Chemical and biological characterization of two FK506 analogs produced by targeted gene disruption in Streptomyces sp. MA6548. J Antibiot (Tokyo). 50(5):418–23.

The invention having now been described by way of written description and example, those of skill in the art will recognize that the invention can be practiced in a variety of embodiments and that the foregoing description and examples are for purposes of illustration and not limitation of the following claims.

What is claimed is:

1. A recombinant *Streptomyces hygroscopicus* host cell that produces 17-desmethylrapamycin, wherein the cell comprises a modified rapamycin polyketide synthase (PKS) gene cluster expressing a modified rapamycin PKS, and wherein said modified rapamycin PKS comprises an acyltransferase (AT) domain in extender module 10 having malonyl CoA specificity.

* * * * *

SEQUENCE LISTING

<160> NUMBER OF SEQ ID NOS: 9

<210> SEQ ID NO 1
<211> LENGTH: 38
<212> TYPE: DNA
<213> ORGANISM: Artificial Sequence
<220> FEATURE:
<223> OTHER INFORMATION: primer

<400> SEQUENCE: 1
atcggatccg cgccaggtcc ggcgacccgt ccgcttcc                                  38

<210> SEQ ID NO 2
<211> LENGTH: 39
<212> TYPE: DNA
<213> ORGANISM: Artificial Sequence
<220> FEATURE:
<223> OTHER INFORMATION: primer

<400> SEQUENCE: 2
gatagatcta gaccgaaggc cgacatcacg gtgtcgaac                                 39

<210> SEQ ID NO 3
<211> LENGTH: 39
<212> TYPE: DNA
<213> ORGANISM: Artificial Sequence
<220> FEATURE:
<223> OTHER INFORMATION: primer

<400> SEQUENCE: 3
atcaagcttg cttgatgtca cgctggcaca gaaccttgg                                 39

<210> SEQ ID NO 4
<211> LENGTH: 39
<212> TYPE: DNA
<213> ORGANISM: Artificial Sequence
<220> FEATURE:
<223> OTHER INFORMATION: primer

<400> SEQUENCE: 4
gatatgcatc cgtgccgtcc caggttctcg gcaccgatc                                 39

<210> SEQ ID NO 5
<211> LENGTH: 50
<212> TYPE: DNA
<213> ORGANISM: Artificial Sequence
<220> FEATURE:
<223> OTHER INFORMATION: primer

<400> SEQUENCE: 5
tggatccaca gatctgcctg cagcatctag aaagcttaca tgcatcctag                     50

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
cgggcgtctg atcgaccagg atgagatggg                                           30

```
<210> SEQ ID NO 7
<211> LENGTH: 40
<212> TYPE: DNA
<213> ORGANISM: Artificial Sequence
<220> FEATURE:
<223> OTHER INFORMATION: primer

<400> SEQUENCE: 7
tatgttggtg tcattctacc agaatcggca aaagatgtca                    40

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
gcgagggcgt agccccggcg                                          20

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
gtcgacctgc aggcatgcaa gctt                                     24
```